(12) United States Patent
Nihalani

(10) Patent No.: US 8,357,081 B2
(45) Date of Patent: Jan. 22, 2013

(54) METHOD AND APPARATUS FOR GASTRIC RESTRICTION OF THE STOMACH TO TREAT OBESITY

(75) Inventor: Raj Nihalani, Irvine, CA (US)

(73) Assignee: Onciomed, Inc., Irvine, CA (US)

( * ) Notice: Subject to any disclaimer, the term of this patent is extended or adjusted under 35 U.S.C. 154(b) by 860 days.

(21) Appl. No.: 12/328,979

(22) Filed: Dec. 5, 2008

(65) Prior Publication Data

US 2010/0145370 A1    Jun. 10, 2010

(51) Int. Cl.
*A61F 2/04* (2006.01)
(52) U.S. Cl. .......................................... 600/37; 606/151
(58) Field of Classification Search .............. 600/29, 600/30, 31, 32, 37, 19, 20; 606/14, 157, 606/191, 201, 202; 450/115, 116, 117, 154, 450/155; 2/311, 321
See application file for complete search history.

(56) References Cited

U.S. PATENT DOCUMENTS

| | | | |
|---|---|---|---|
| 4,403,604 A | 9/1983 | Wilkinson et al. | |
| 4,592,339 A | 6/1986 | Kuzmak et al. | |
| 4,696,288 A | 9/1987 | Kuzmak et al. | |
| 4,739,758 A | 4/1988 | Lai et al. | |
| 5,074,868 A | 12/1991 | Kuzmak | |
| 5,129,915 A | 7/1992 | Cantenys | |
| 5,449,368 A * | 9/1995 | Kuzmak | 606/157 |
| 5,514,155 A * | 5/1996 | Daneshvar | 606/201 |
| 5,601,604 A | 2/1997 | Vincent | |
| 5,910,149 A * | 6/1999 | Kuzmak | 606/157 |
| 5,938,669 A | 8/1999 | Klaiber et al. | |
| 6,146,240 A * | 11/2000 | Morris | 450/97 |
| 6,511,490 B2 | 1/2003 | Robert | |
| 6,547,801 B1 | 4/2003 | Dargent et al. | |
| 6,558,400 B2 | 5/2003 | Deem et al. | |
| 6,656,194 B1 | 12/2003 | Gannoe et al. | |
| 6,676,674 B1 | 1/2004 | Dudai | |
| 6,746,460 B2 | 6/2004 | Gannoe et al. | |
| 6,755,869 B2 | 6/2004 | Geitz | |
| 6,773,440 B2 | 8/2004 | Gannoe et al. | |
| 6,981,978 B2 | 1/2006 | Gannoe | |
| 6,994,715 B2 | 2/2006 | Gannoe et al. | |
| 7,033,373 B2 | 4/2006 | de la Torre et al. | |
| 7,033,384 B2 | 4/2006 | Gannoe et al. | |
| 7,083,629 B2 | 8/2006 | Weller et al. | |
| 7,097,650 B2 | 8/2006 | Weller et al. | |
| 7,101,381 B2 * | 9/2006 | Ford et al. | 606/151 |
| 7,175,638 B2 | 2/2007 | Gannoe et al. | |
| 7,211,094 B2 | 5/2007 | Gannoe et al. | |
| 7,214,233 B2 | 5/2007 | Gannoe et al. | |
| 7,220,237 B2 | 5/2007 | Gannoe et al. | |
| 7,229,428 B2 | 6/2007 | Gannoe et al. | |

(Continued)

FOREIGN PATENT DOCUMENTS

| | | |
|---|---|---|
| CN | 101193610 | 6/2008 |
| EP | 1205148 | 5/2002 |

(Continued)

*Primary Examiner* — John Lacyk
*Assistant Examiner* — Joshua D Lannu
(74) *Attorney, Agent, or Firm* — Snell & Wilmer LLP

(57) ABSTRACT

The invention generally relates to a method and apparatus to treat obesity. In an exemplary embodiment, the invention relates to tucking a portion of the greater curvature of the stomach inwards, and covering the stomach around the greater curvature and lesser curvature with a silicone skirt to induce satiety and reduce the volume of the stomach body.

19 Claims, 26 Drawing Sheets

U.S. PATENT DOCUMENTS

| | | | |
|---|---|---|---|
| 7,288,099 B2 | 10/2007 | Deem et al. | |
| 7,288,101 B2 | 10/2007 | Deem et al. | |
| 7,306,614 B2 | 12/2007 | Weller et al. | |
| 7,338,433 B2 | 3/2008 | Coe | |
| 7,367,937 B2 | 5/2008 | Jambor et al. | |
| 2003/0105469 A1* | 6/2003 | Karmon | 606/92 |
| 2003/0120288 A1 | 6/2003 | Benchetrit | |
| 2003/0158564 A1 | 8/2003 | Benchetrit | |
| 2003/0208212 A1 | 11/2003 | Cigaina | |
| 2004/0044354 A1 | 3/2004 | Gannoe et al. | |
| 2004/0088008 A1 | 5/2004 | Gannoe et al. | |
| 2004/0122452 A1 | 6/2004 | Deem et al. | |
| 2004/0122453 A1 | 6/2004 | Deem et al. | |
| 2005/0096638 A1 | 5/2005 | Starkebaum | |
| 2005/0119674 A1* | 6/2005 | Gingras | 606/151 |
| 2005/0159769 A1 | 7/2005 | Alverdy | |
| 2005/0251181 A1 | 11/2005 | Bachmann | |
| 2006/0212053 A1* | 9/2006 | Gertner | 606/153 |
| 2007/0015955 A1 | 1/2007 | Tsonton | |
| 2007/0027356 A1 | 2/2007 | Ortiz | |
| 2007/0048334 A1 | 3/2007 | Aurora | |
| 2007/0083224 A1 | 4/2007 | Hively | |
| 2007/0100367 A1 | 5/2007 | Quijano et al. | |
| 2007/0112364 A1 | 5/2007 | Gerbi et al. | |
| 2007/0118168 A1 | 5/2007 | Lointier et al. | |
| 2007/0135829 A1 | 6/2007 | Paganon | |
| 2007/0156013 A1 | 7/2007 | Birk | |
| 2007/0233161 A1 | 10/2007 | Weller et al. | |
| 2007/0250083 A1 | 10/2007 | Deem et al. | |
| 2007/0265645 A1 | 11/2007 | Birk et al. | |
| 2008/0033574 A1 | 2/2008 | Bessler et al. | |
| 2008/0091076 A1 | 4/2008 | Roth et al. | |
| 2008/0091077 A1 | 4/2008 | Roth et al. | |
| 2008/0091078 A1 | 4/2008 | Roth et al. | |
| 2008/0091079 A1 | 4/2008 | Roth et al. | |
| 2008/0132925 A1 | 6/2008 | Demarais | |
| 2008/0208240 A1 | 8/2008 | Paz | |
| 2008/0208241 A1 | 8/2008 | Weiner et al. | |
| 2008/0208355 A1 | 8/2008 | Stack et al. | |
| 2008/0243166 A1 | 10/2008 | Paganon et al. | |
| 2009/0118756 A1 | 5/2009 | Valencon et al. | |

FOREIGN PATENT DOCUMENTS

| | | |
|---|---|---|
| GR | 1002464 | 11/1996 |
| GR | 2007/0100015 | 9/2008 |
| WO | WO 01/41671 | 6/2001 |
| WO | WO 2004/014245 | 2/2004 |
| WO | WO 2008/122713 | 10/2008 |
| WO | WO 2009/059803 | 5/2009 |

* cited by examiner

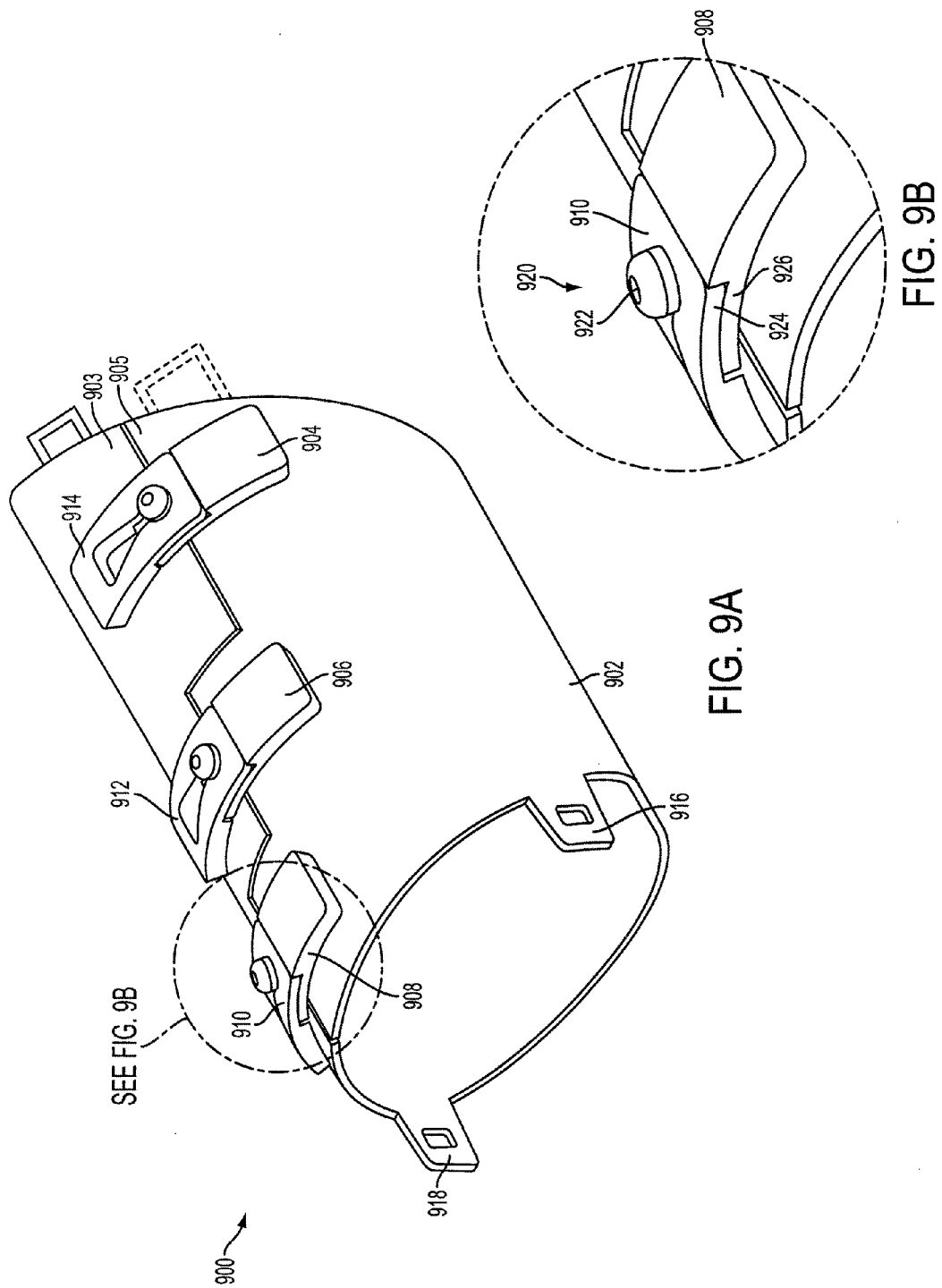

METHOD AND APPARATUS FOR GASTRIC RESTRICTION OF THE STOMACH TO TREAT OBESITY

BACKGROUND

1. Field

The invention relates to a method and apparatus for treating obesity and controlling weight gain in mammals, and more specifically, to a gastric skirt placed around the stomach to cause a reduced desire for eating for treating obesity and controlling weight gain in mammals.

2. Related Art

Extreme obesity is a major illness in the United States and other developed countries. More than half of Americans are overweight, while nearly one-third are categorized as obese. Obesity is the accumulation of excess fat on the body, and is defined as having a body mass index (BMI) of greater than 30. Many serious long-term health consequences are associated with obesity, such as, hypertension, diabetes, coronary artery disease, stroke, congestive heart failure, venous disease, multiple orthopedic problems and pulmonary insufficiency with markedly decreased life expectancy.

Medical management of obesity including dietary, psychotherapy, medications and behavioral modification techniques have yielded extremely poor results in terms of treating obesity. Several surgical procedures have been tried which have bypassed the absorptive surface of the small intestine or have been aimed at reducing the stomach size by either partition or bypass. These procedures have been proven both hazardous to perform in morbidly obese patients and have been fraught with numerous life-threatening postoperative complications. Moreover, such operative procedures are often difficult to reverse.

One procedure for treating morbid obesity is referred to as a "biliopancreatic diversion." Biliopancreatic diversion surgery is a reduction of the stomach volume and a diversion of food from the stomach to the final segment of the small intestine, bypassing the beginning and middle portions of the small intestine to limit the amount of nutrients and calories absorbed by the body. This procedure removes about one half of the stomach, and then connects the stomach to the last 250 cm of the small intestine. Some disadvantages of this surgery include patients suffering from protein malnutrition, anemia, gastric retention, diarrhea, abdominal bloating, and intestinal obstruction.

Another bariatric surgery, "gastric bypass," is a bypass connecting the lower compartment of the stomach to the initial portion of the small intestine. This procedure limits the amount of food that can be ingested at one sitting and reduces absorption of food across the small intestine. In addition to surgical complications, patients may also suffer from acute gastric dilation, anastomotic leak, anemia, and dumping syndrome.

Yet another bariatric surgical procedure is "vertical-banded gastroplasty," which restricts the volume of the stomach by using staples. In this procedure, staples are placed in the upper stomach region to create a small pouch with a narrow outlet to the remaining portion of the stomach. A band is placed around the narrow outlet to provide support and inhibit stretching of the stomach. In addition to surgical complications, patients undergoing this procedure may suffer from vomiting, ulcers, band erosion, and leaks.

Recently, minimally invasive procedures and devices which create a feeling of early satiety have been introduced into the marketplace in an attempt to address some of the issues above. The LAP-BAND® is a band which encircles the stomach at the region of the fundus-cardia junction; it is a restrictive procedure similar to stomach stapling. The procedure requires general anesthesia, a pneumoperitoneum, muscle paralysis, and extensive dissection of the stomach at the region of the gastro esophageal junction. The procedure also requires continual adjustment of the band, or restriction of a portion of the device. Although less invasive than other bariatric surgical procedures and potentially reversible, the LAP-BAND® does not reduce the volume of the stomach by any great extent and some patients report a feeling of hunger most of the time. Furthermore, once implanted, the LAP-BAND®, although it is adjustable by percutaneous means, may require many iterative adjustments before it is optimally positioned. In addition, the port used to adjust the LAP-BAND® is left inside the patient's body.

Therefore, there is a need for minimally-invasive procedures and devices that eliminate the above-mentioned drawbacks of conventional methods and devices that are currently being used to treat obesity.

SUMMARY

In one embodiment, the invention includes: a sheet having a top portion, a bottom portion, a left portion, and a right portion; a first connector attached to the right portion of the sheet; a second connector attached to the left portion of the sheet; a first attachment wing attached to the top portion of the sheet; a connector having an upper portion and a lower portion, the lower portion of the connector attached to the first attachment wing; a strap having a distal end and a proximal end; and a second attachment wing attached to the distal end of the strap, the second attachment wing also attached to the upper portion of the connector.

In one embodiment, the invention includes a gastric constriction device for treating obesity in mammals. The device includes an elastomeric sheet formed in the shape of a cylinder and having a top portion, a bottom portion, a left portion, and a right portion, the sheet configured to be wrapped around a tucked-in stomach of a mammal so that the left portion is in contact with the right portion when the sheet is wrapped around the stomach. The device may also include a first connector attached to the right portion of the sheet, a second connector attached to the left portion of the sheet, the second connector attachable to the first connector, a connecting strap having an upper portion and a lower portion, the lower portion of the connecting strap configured to be attached to the top portion of the sheet, and a collar configured to be attached to the upper portion of the connecting strap, the collar further configured to be placed around an esophagus of the mammal.

BRIEF DESCRIPTION OF THE DRAWINGS

These and other embodiments of the invention will be discussed with reference to the following exemplary and non-limiting illustrations, in which like elements are numbered similarly, and where:

FIG. 9A is a view of a folded gastric skirt with locking clips;

FIG. 9B is a view of a locking clip for a gastric skirt;

DETAILED DESCRIPTION

Figure 1A:
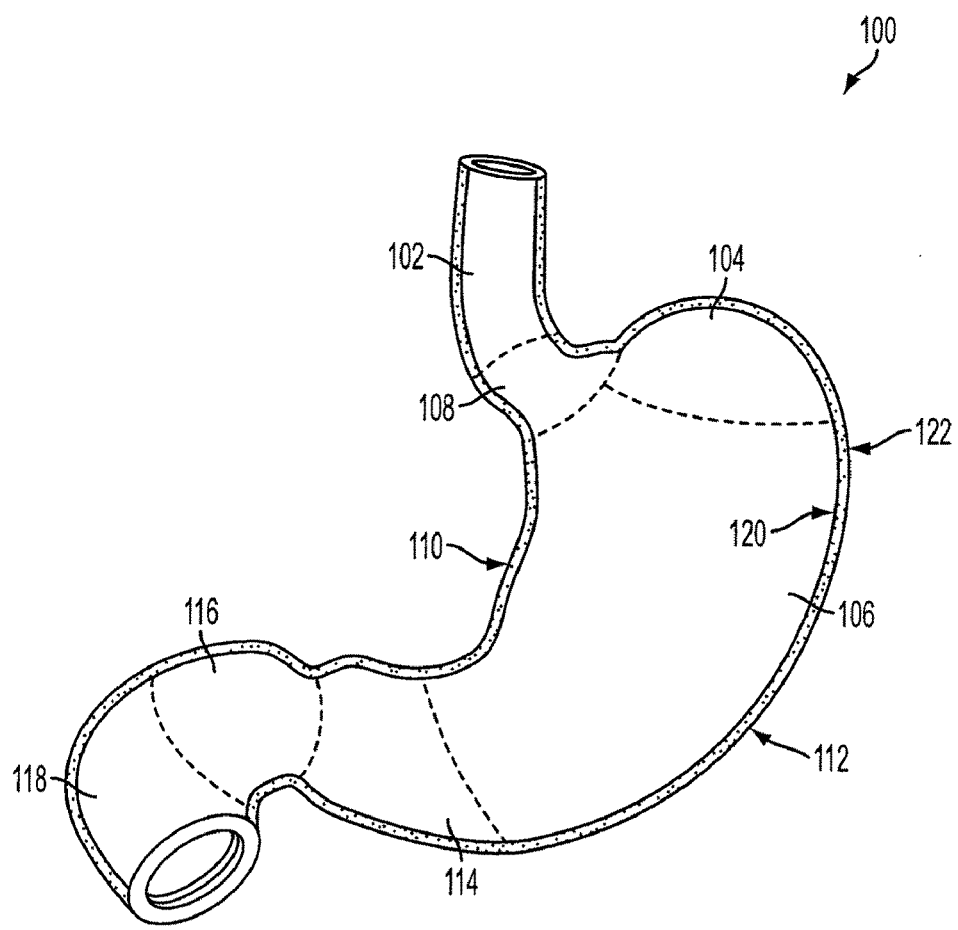
FIG. 1A is a view of a stomach of a mammal.

FIG. 1A is a view of a stomach 100 of a mammal (e.g., human). As shown in FIG. 1A, the stomach 100 has at least two curvatures, a lesser curvature 110 and a greater curvature 112. The cardia or proximal stomach 108 is located in the upper left portion of the stomach 100 and serves as the junction between the esophagus 102 and the body of the stomach 106. The fundus 104 is located in the upper right portion of the stomach 100. The lower portion of the stomach 100 is known as the distal stomach and includes the antrum 114 and the pylorus 116. The antrum 114 is where food is mixed with gastric juices. The pylorus 116 has a muscular pyloric sphincter that acts as a valve to control emptying of the stomach contents into the proximal segment of the small intestine 118 (partially shown). The inner lining 120 of the stomach 100 separates the body 106 from the outer wall 122.

The invention is directed to a gastric skirt that is placed around the stomach 100 by a healthcare professional, such as a surgeon, a bariatric surgeon or a gastrointestinal specialist trained in laparoscopic and/or general surgery procedures. The gastric skirt can be positioned using a routine laparoscopic procedure or a conventional open-surgical procedure. Furthermore, the gastric skirt can be placed around the stomach 100 using newer techniques, methods and procedures for laparoscopic surgery.

The invention can be utilized in conjunction with the LAP-BAND® procedure and/or other post-gastric bypass procedures such as gastric sleeve procedure treatments that provide reinforcement and restraining devices to prevent further expansion or re-expansion of the stomach 100.

Figure 1B:
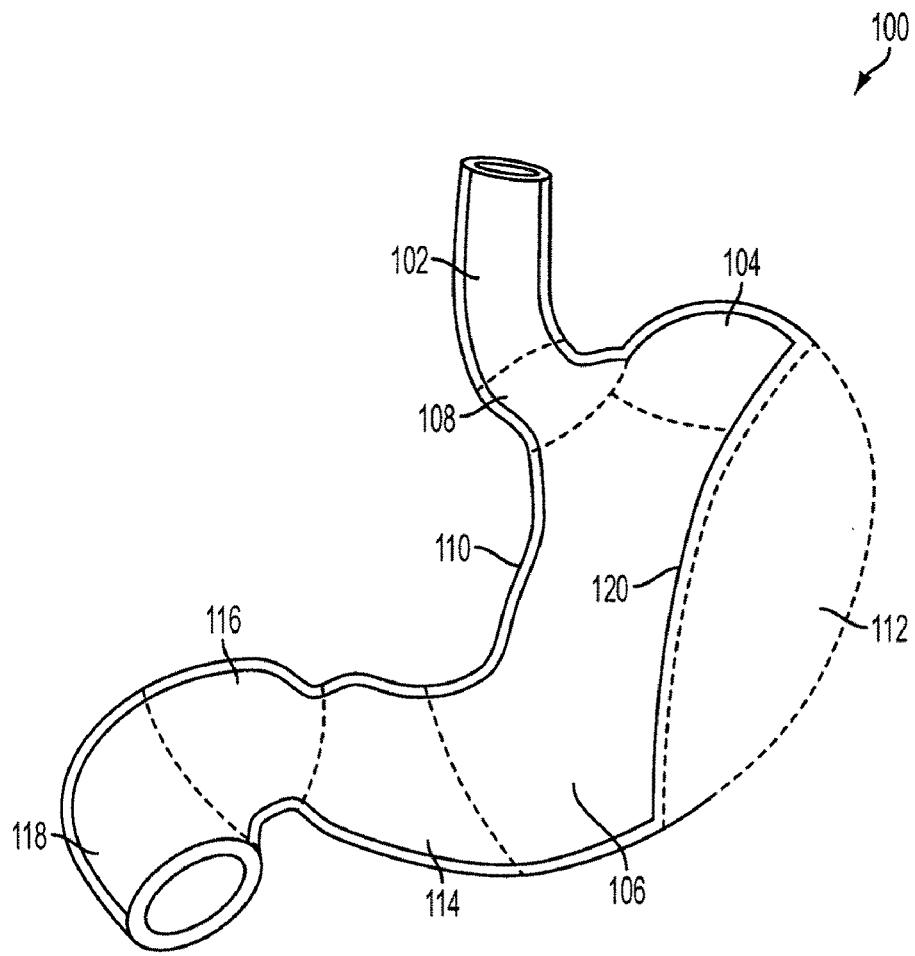
FIG. 1B is a view of a partially tucked-in stomach of a mammal.

FIG. 1B is a view of a partially tucked-in stomach 100 of a human. Prior to placing the gastric skirt around the stomach 100, a linear portion of the greater curvature 112 is tucked inwards into the stomach 100. As shown in FIG. 1B, the inner lining 120 is depressed within the stomach 100 as a result of the tucking procedure, and the tucked-in portion occupies space within the stomach 100. Thus, the internal volume of the stomach 106 is substantially decreased, creating a ridge like effect, leading to the slowing of the passage of food, and thus less food consumption, while still enabling absorption of vital fluids and nutrients (unlike a gastric bypass procedure). In addition, the internal volume of the fundus 104 is reduced.

In another embodiment, the tucked-in portion of the stomach 100 may be a linear portion of the lesser curvature 110, a portion of the body 106, or a portion of the fundus 104, not along either the greater curvature 112 or the lesser curvature 110. Therefore, any portion of the stomach 100 may be tucked-in and wrapped using the gastric skirts disclosed herein.

Figure 2A:
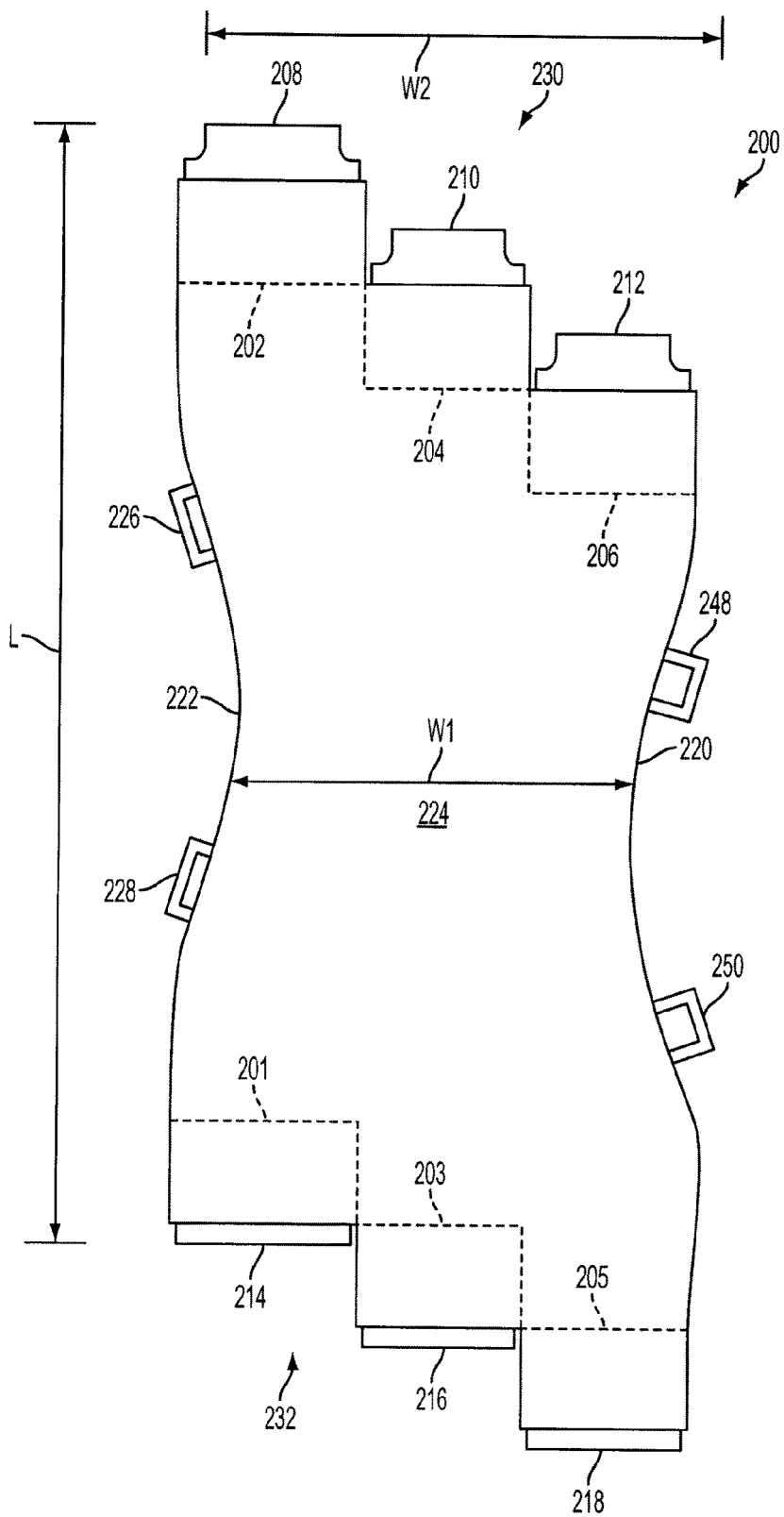
FIG. 2A is a view of a laid-open gastric skirt.

FIG. 2A is a view of a laid-open gastric skirt 200. The gastric skirt 200 may be formed as a sheet 224 prior to being wrapped around a patient's stomach. For illustrative purposes, the gastric skirt 200 has a left side 232, a right side 230, a bottom portion 220, and a top portion 222. Each connector 208, 210, and 212 may be offset or staggered relative to its adjacent connector. Similarly, each receiver 214, 216, and 218 may be offset or staggered relative to its adjacent receiver. In one embodiment, each offset may be approximately 1-3 centimeters. The bottom portion 220 and the top portion 222 may have an inward curved or concave edge. The gastric skirt 200 may have a length L of approximately 6-16 centimeters, a central width W1 of approximately 3-7 centimeters, and an outer width W2 of approximately 6-10 centimeters.

In a preferred embodiment, the length L is at least 8 centimeters, the central width W1 is at least 4 centimeters, and the outer width W2 is at least 7 centimeters.

The gastric skirt 200 may have a staggered step design and may be formed in the shape of a parallelogram when laid-open, where the opposing ends of the gastric skirt 200 interconnect in a stepped fashion when the gastric skirt 200 is folded. For example, step element 201 is staggered relative to immediately opposing step element 202. Likewise, step element 203 and step element 205 are staggered relative to their immediately opposing step elements 204 and 206, respectively. When the gastric skirt 200 is wrapped or folded into position around a patient's stomach 100, the opposing step elements interconnect with each other, forming the end at the greater curvature 112 and the gastric skirt 200 is formed into a conical cylindrical shape, which is described in more detail below.

Attached to each step element is a male connector or a female receiver or vice versa. In the exemplary embodiment, a male connector 208 is attached to a female receiver 214. When the gastric skirt 200 is folded into position, the male connector 208 couples with the female receiver 214. The male connectors 210 and 212 couple with the female receivers 216 and 218, respectively, when the gastric skirt 200 is wrapped or folded into position around the stomach. In other embodiments, the gastric skirt 200 may have one set of connectors (e.g., a single male connector 208 and a single female receiver 214) or two sets of connectors (e.g., 2 male connectors 208 and 210 and 2 female receivers 214 and 216). The connectors can be of various shapes and sizes, and are not limited to the connector design shown in FIG. 2A. Furthermore, the connectors can be positioned at various locations on the gastric skirt 200, and are not limited to being positioned at the left side 232 and the right side 230 of the gastric skirt 200.

The gastric skirt 200 has a bottom portion 220 that is inward curving. Opposite the bottom portion 220, the gastric skirt 200 has a top portion 222 that is inward curving. When the gastric skirt 200 is folded into position, the bottom and top portions 220 and 222 come into contact with the lesser curvature 110 and provide the gastric skirt 200 with a contoured, conical shape. The conical shape allows the gastric skirt 200 to properly fit around the stomach 100.

Furthermore, one or more optional connectors or wings 226 and 228 are attached to the top portion 222 of the gastric skirt 200 and one or more optional connectors or wings 248 and 250 are attached to the bottom portion 220 of the gastric skirt 200. The connectors or wings 226 and 228 may be used to attach the gastric skirt 200 to collar connector straps (shown in FIGS. 10A, 10B, and 11). The connectors or wings 248 and 250 may be used to attach the gastric skirt 200 to connector straps (shown in FIG. 11).

The body or sheet 224 of the gastric skirt 200 is relatively flexible and may be made of an elastic polymer ("elastomer"), such as, but not limited to, silicone, polypropylene, polyethylene terephthalate, polytetrafluoroethylene, polyaryletherketone, nylon, fluorinated ethylene propylene, polybutester, or any combination thereof. Furthermore, the elastomer may be non-porous. Alternatively, the elastomer may be microporous or porous to allow for better expansibility and oxygenation and for tissue in-growth to better hold the gastric skirt 200 in place.

In a preferred embodiment, the elastomer is silicone. Silicone provides an ample amount of rigidity, while still providing flexibility to accommodate changes in stomach shape and size during peristalsis. A silicone body may be preferred over a porous body, as larger pores may allow the stomach muscles or tissue to seep through and grow onto the outside of the body 224. This overgrowth of the stomach through the body 224 may make it difficult to remove the gastric skirt 200 from the patient if needed. Furthermore, the silicone allows some expandability of the stomach 100, which is the stomach's natural function. Thus, the gastric skirt 200 allows the stomach to accommodate some gases and larger pieces of food or meat.

Alternatively, more rigid materials, such as Teflon®, Dacron® or ePTFE or Teflon or wire mesh may be used if they provide an adequate level of flexibility, and do not significantly irritate or erode the stomach surface. That is, the gastric skirt 200 should be relatively flexible, as a very rigid stomach wrap may cause discomfort to the patient, as well as injury to the stomach and other gastric organs. The gastric skirt 200 is tightly positioned around the tucked-in stomach so little to no open space is provided between the gastric skirt 200 and the outer surface of the stomach.

In another embodiment, the body 224 of the gastric skirt 200 may be made of a biodegradable and absorbable polymer or copolymer, such as, but not limited to, polyglycolic acid (PGA), polylactic acid (PLA), polycaprolactone, polyhydroxyalkanoate, various thermoplastic materials, or any combination thereof. Once placed around the stomach 100, the gastric skirt 200 stays in position for a predetermined amount of time. After the predetermined amount of time has elapsed, the gastric skirt 200 may be absorbed by the patient's bodily fluids, eliminating the need for a second procedure to remove the gastric skirt 100. In this particular embodiment, the entire gastric skirt 200, including the male connectors and the female receivers, are made of a biodegradable material.

The staggered step design allows the gastric skirt 200, including all of the connectors and receivers, to be rolled into a highly compact fashion. In one embodiment, the gastric skirt 200 can be placed around a patient's stomach using a routine laparoscopic procedure, referred to as a laparoscopy. During a laparoscopy, the gastric skirt 200 is inserted into the patient via a trocar through a hole made in the patient's abdomen. The staggered step design minimizes the diameter of the gastric skirt 200 when it is rolled for insertion through the trocar. That is, the connectors and receivers are not positioned on top of each other in the rolled position to minimize the thickness for insertion.

In another embodiment, male connectors are connected to their respective female receivers with an elastic material. For example, male connector 208 is connected to female receiver 214 with a strap made from an elastic material. The strap is positioned within an internal channel that runs lengthwise from the left side 232 to the right side 230 within the gastric skirt 200. The strap is preferably made of a more elastic material than the gastric skirt 200 so that the connectors can accommodate peristalsis and movement of the stomach. This embodiment allows stress to be placed on the strap rather than the gastric skirt 200, thereby preventing the gastric skirt 200 from being overstretched due to peristalsis.

Figure 2B:
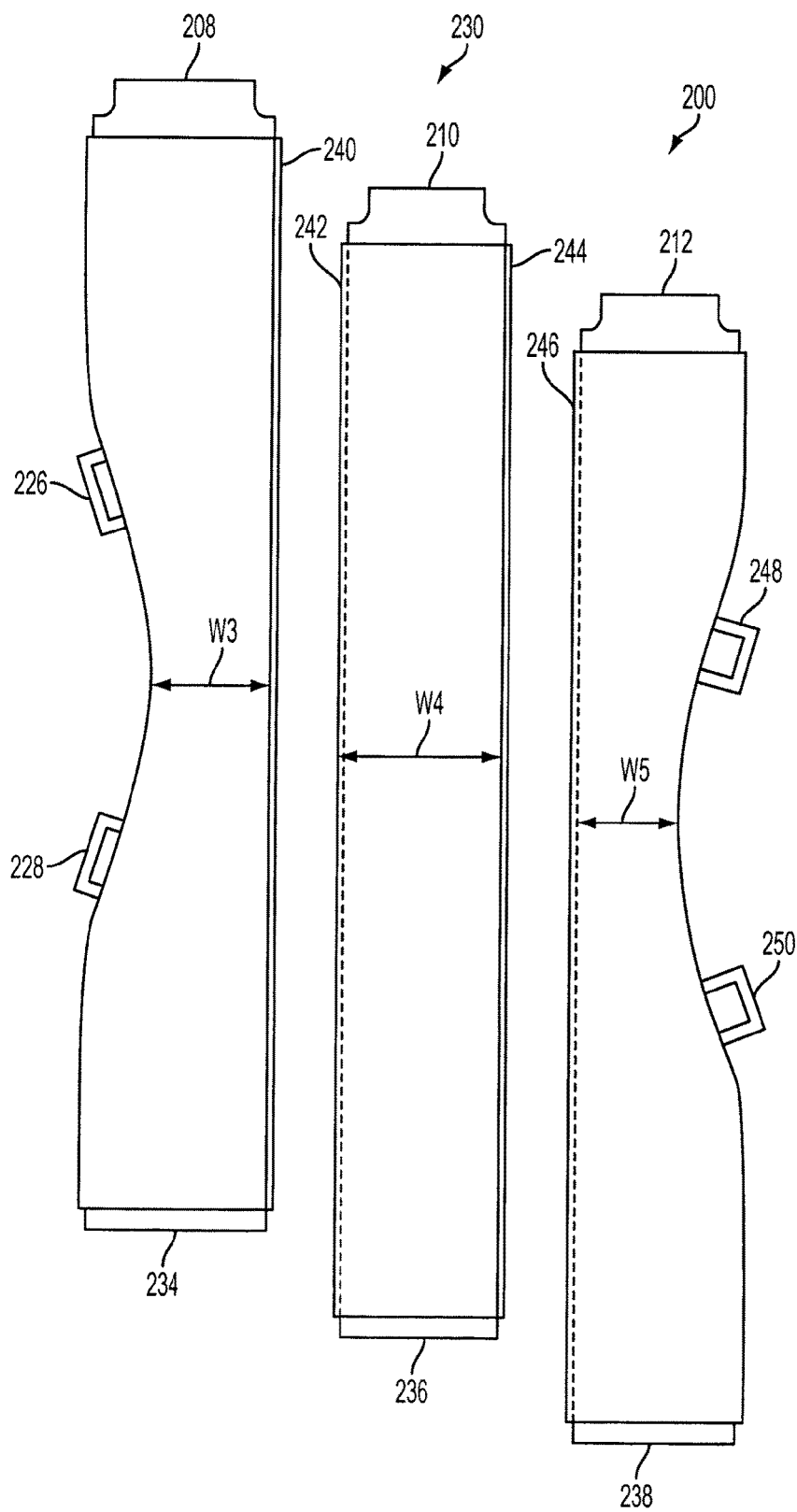
FIG. 2B is a view of a modular laid-open gastric skirt.

FIG. 2B is a view of a modular laid-open gastric skirt 200. The modular gastric skirt 200 may have two or more rectangular strips or modules 234, 236, and 238. Each strip may have a ridge 240 (and 244) and/or a groove 242 (and 246) for attachment to adjacent strips. The ridge 240 securely fits into the groove 242 along the length of each strip to prevent unwanted detachment of adjacent strips and any in-growth of tissue between adjacent strips. Some advantages of the strips include each strip can be inserted separately and the size of the gastric skirt 200 can be adjusted at the time of surgery to account for the amount of tucking, size and orientation of the stomach 100. The modular gastric skirt 200 may have a width W3 of approximately 1-3 centimeters, a width W4 of approximately 1-4 centimeters, and a width W5 of approximately 1-3 centimeters. The widths may vary depending on the size and amount of tucking needed. The modular gastric skirt 200 may have a length L of approximately 6-16 centimeters.

In an embodiment, the modular gastric skirt 200 may have utilize only two of the rectangular strips or modules 234, 236, and 238. For example, module 234 can be connected to module 236 to form the modular gastric skirt 200. Alternatively, module 234 can be connected to module 238 to form the modular gastric skirt 200.

Figure 3:
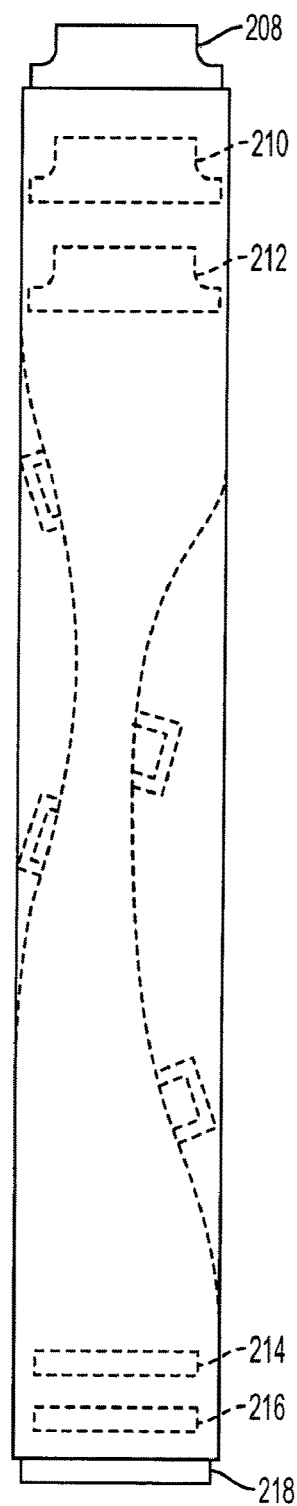
FIG. 3 is a view of a rolled gastric skirt.

FIG. 3 is a view of a rolled gastric skirt 300. The gastric skirt 300 is tightly rolled so that it can be inserted through a trocar as described above or other means. The staggered step design allows the male connectors 208, 210, and 212, and the female connectors 214, 216, and 218 to not overlap with each other when the gastric skirt 300 is rolled. By not overlapping, the male connectors 208, 210, and 212 and the female receivers 214, 216, and 218 are evenly flush with each other, so the diameter of the rolled gastric skirt 300 is minimized. Similarly, the connectors, the cardia collar and the antral collar may be passed through the trocar into the stomach for connection to the gastric skirt 200.

Figure 4:
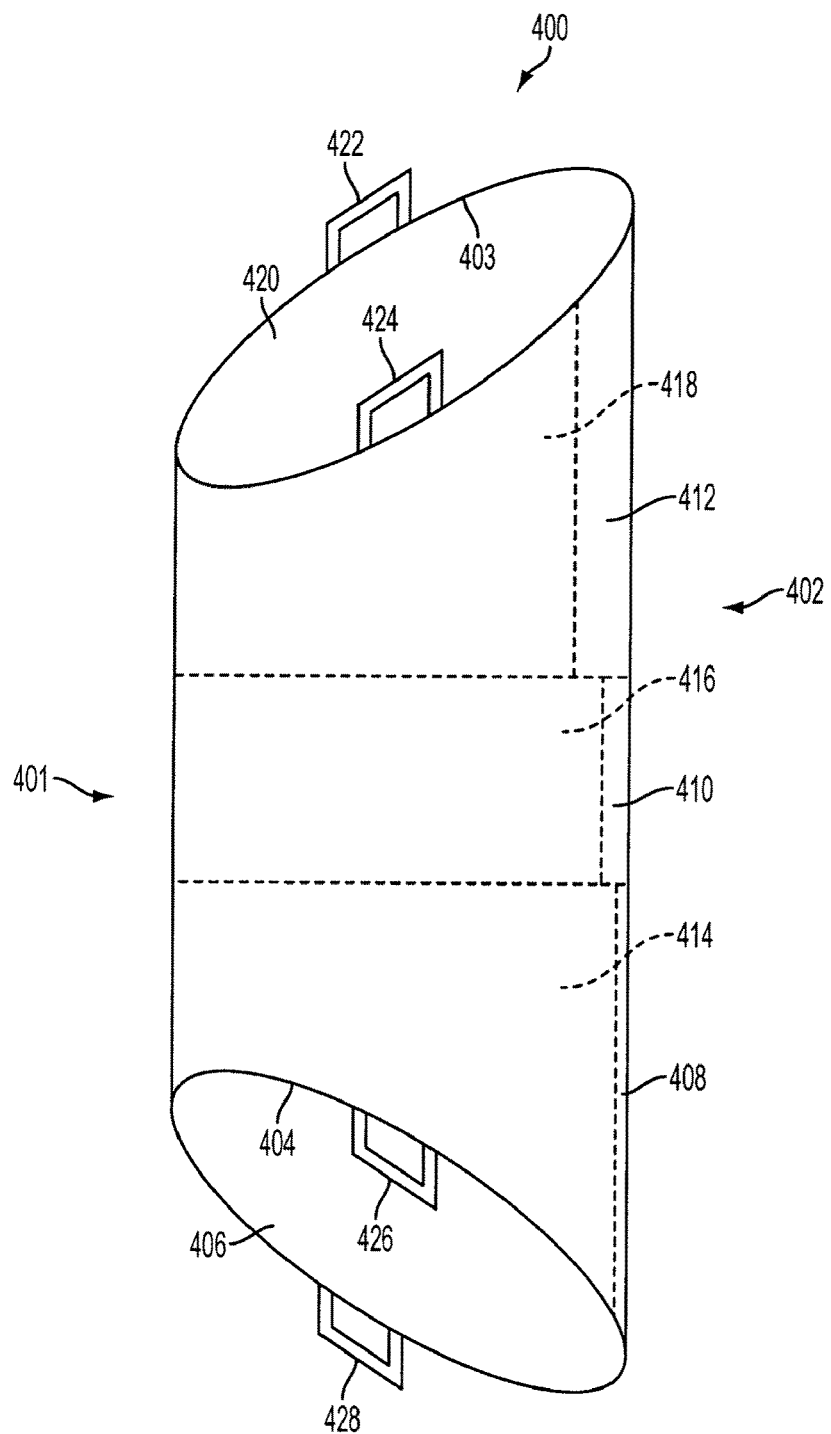
FIG. 4 is a view of a folded conical cylinder-shaped gastric skirt.

FIG. 4 is a view of a folded conical cylinder-shaped gastric skirt 400. As shown, step elements 412, 410, and 408 are each connected to their immediately opposing step elements 418, 416, and 414, respectively, to form a conical cylinder-shaped gastric skirt 400. In an embodiment, the outer or upper curvature 403 has a convex shape and is outwardly curving. The inner or lower curvature 404 has a concave shape and is inwardly curving. The conical cylinder shape allows the gastric skirt 400 to properly fit around and contact the stomach. The upper portion of the stomach 100 is covered by the gastric skirt 400 near the upper curvature 403, as the upper portion of the stomach has a larger diameter than the lower portion of the stomach. The lower portion of the stomach is covered by the gastric skirt 400 near the lower curvature 404.

The diameter of the upper curvature opening 420 (i.e., cardia end) and the lower curvature opening 406 (i.e., antral end) are similar. The gastric skirt 400 can be a "one-size fits all" design, where a single-sized gastric skirt 400 is used for all or most stomach sizes. To adjust to a "one-size fits all" gastric skirt 400, the stomach is tucked in per physician's preference and the gastric skirt 400 is simply tightened accordingly when it is being positioned around the stomach.

Furthermore, the one or more optional wings 422 and 424 are attached on the circumference of the upper curvature 403. The wings 422 and 424 are used to attach the gastric skirt 400 to collar connector straps (see also FIGS. 10A and 10B). Similarly, the circumference of the lower curvature 404 can also have one or more wings 426 and 428 attached. In another embodiment, the gastric skirt 400 can have no wings attached, or wings only on one side, either on the upper curvature 403 or the lower curvature 404.

In another embodiment, a healthcare professional can estimate or measure the size of the patient's stomach beforehand. Using this measurement, the gastric skirt 400 can be tailored to provide a customized fit (for example, 10-30% smaller in diameter than the measurement to accommodate the tuck). The prior measurement reduces the risk of overtucking or overstretching or damaging the gastric skirt 400 when it is being positioned around the stomach, and can allow for a smooth and even customized fit (see also FIGS. 5A, 5B, and 5C).

This conical cylinder design allows a single gastric skirt to properly hold various portions of the stomach, even though the stomach may vary in size throughout. The use of a single gastric skirt reduces the complexity of the system and reduces the possibility of complications which may arise due to uneven pressure resulting from multiple skirts around the stomach. Alternatively, multiple, separately-sized gastric skirts, such as, one for a larger portion of the stomach, and one for a smaller portion of the stomach, may be used.

Figure 5A:
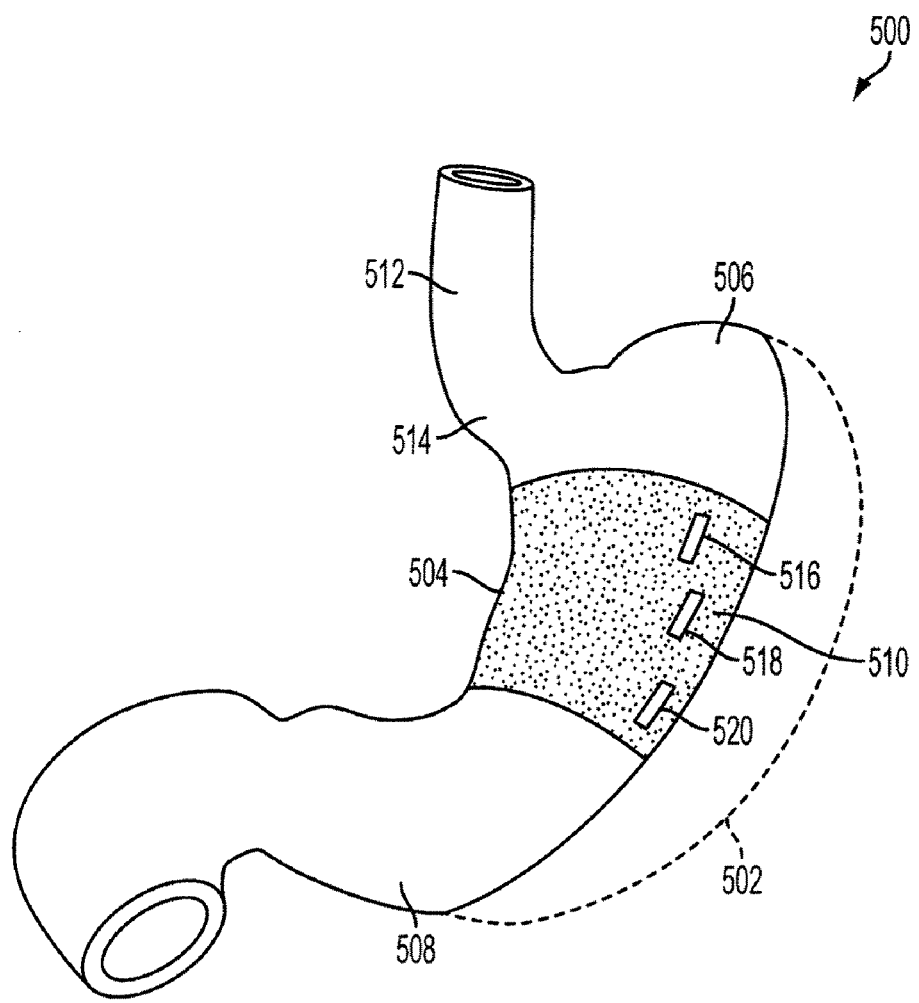
FIG. 5A is a view of a gastric skirt placed in position around a stomach.

FIG. 5A is a view of a gastric skirt 500 placed in position around a stomach. The gastric skirt 510 is designed to cover substantially all of the greater or outer curvature 502, and substantially all of the lesser or inner curvature 504. As shown in FIG. 5A, a portion of the fundus 506 and the antrum/pylorus 508 may be tucked or covered or restricted by the gastric skirt 510.

In another embodiment, the gastric skirt 510 can be designed to cover a smaller portion of the greater curvature 502 and/or a smaller portion of the lesser curvature 504, instead of covering the entire respective surfaces. Furthermore, the gastric skirt 510 can be designed to cover other surfaces of the stomach in addition to the greater curvature 502 and/or the lesser curvature 504. For example, the gastric skirt 510 may have a larger surface area and cover the fundus 506 and/or the antrum/pylorus 508, or portions thereof, in addition to portions of the greater curvature 502 and/or the lesser curvature 504.

Unlike conventional gastric-restraint devices, such as the LAP-BAND®, the gastric skirt 510 is not placed between the cardia 514 and the fundus 506 forming a pouch. Furthermore, the gastric skirt 510 is not placed around the esophagus 512. As described above, the gastric skirt 510 is instead fitted or positioned around the body of the stomach 500 (i.e., around surfaces of the greater curvature 502 and the lesser curvature 504 of the stomach 500).

Figure 5B:
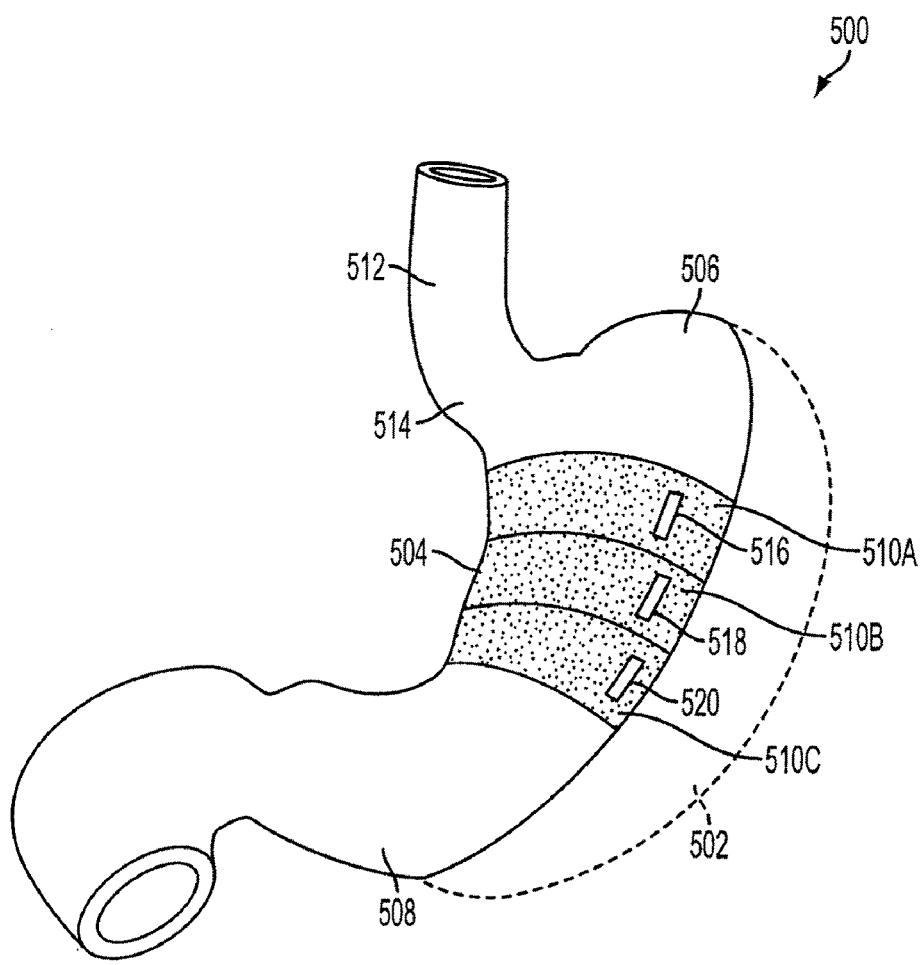
FIG. 5B is a view of a modular gastric skirt placed in position around a stomach.

FIG. 5B is a view of a modular gastric skirt placed in position around a stomach 500. The modular skirt 510 is shown as three strips 510A, 510B, and 510C connected to one another. The male and female connectors are shown as 516, 518, and 520, respectively.

Figure 5C:
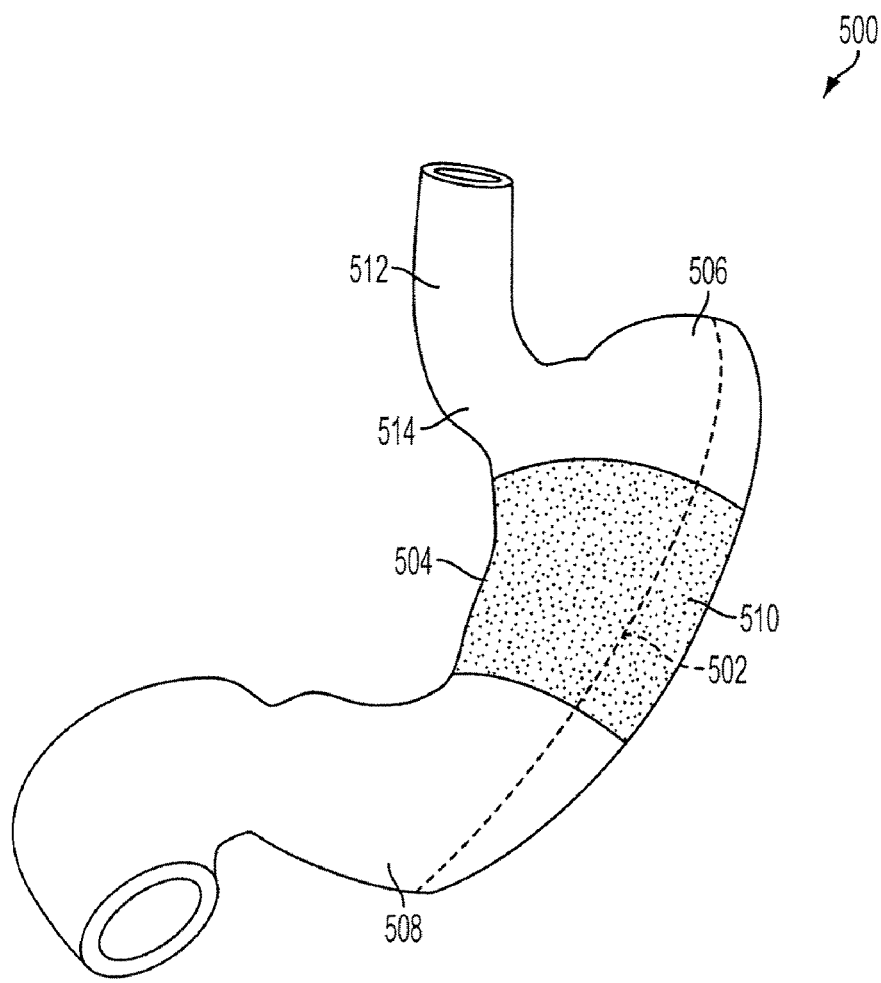
FIG. 5C is a view of a gastric skirt placed in position around a stomach that shows a tucked-in portion of the stomach.

FIG. 5C is a view of a gastric skirt 510 placed in position around a stomach 500 that shows a tucked-in portion of the stomach. In this example, the greater curvature 502 is tucked into the body of the stomach 500 and the gastric skirt 510 is placed around the tucked stomach to secure the tucked portion in place. The tucked portion is pushed into the body of the stomach, thus reducing the internal volume of the stomach.

Figure 6:
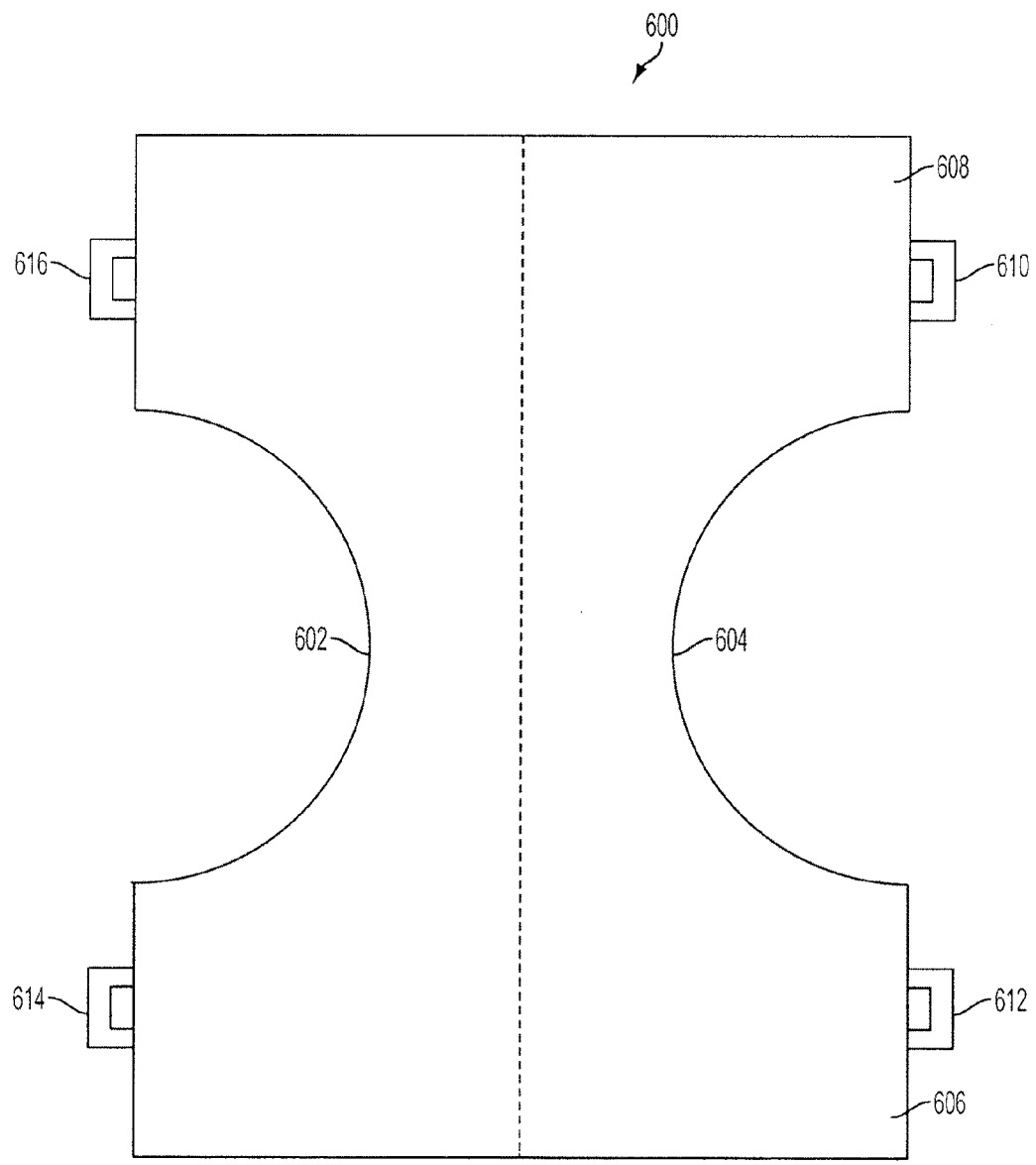
FIG. 6 is a view of a laid-open butterfly-shaped gastric skirt.

FIG. 6 is a view of a laid-open butterfly-shaped gastric skirt 600. The gastric skirt 600 has an indentation 602 on one side and an indentation 604 on the opposing side. The proximal end 606 and the distal end 608 can include connectors and receivers, respectively, so that when the gastric skirt 600 is folded, the proximal end 606 and the distal end 608 can be connected together.

Indentations 602 and 604 can be any shape such as an ellipse, oval, hourglass, or semicircular shape as shown in FIG. 6. For example, each of the indentations 602 and 604 can be formed in the shape of a square, a triangle, an oval, a semi-circle, an ellipse, a wave, a curve, or any other shape that creates an indentation. The size of each indentation 602 and 604 can be varied in order to provide an optimal fit around the stomach. Indentations 602 and 604 do not necessarily have to be the same shape or size as one another.

Furthermore, optional wing 610 is attached on one substantially horizontal portion adjacent to indentation 604, and optional wing 612 is attached on the other substantially horizontal portion adjacent to indentation 604. The wings 610 and 612 are used to attach the gastric skirt 600 to collar connector straps (shown in FIGS. 10A, 10B, and 11). Similarly, the side of the gastric skirt 600 with indentation 602 has wings 614 and 616 attached. In another embodiment, the gastric skirt 600 can have no wings attached, or wings only on one side. The dashed line indicates that the gastric skirt 600 can have two or more modular pieces connected to one another similar to that shown in FIG. 2B.

Figure 7:
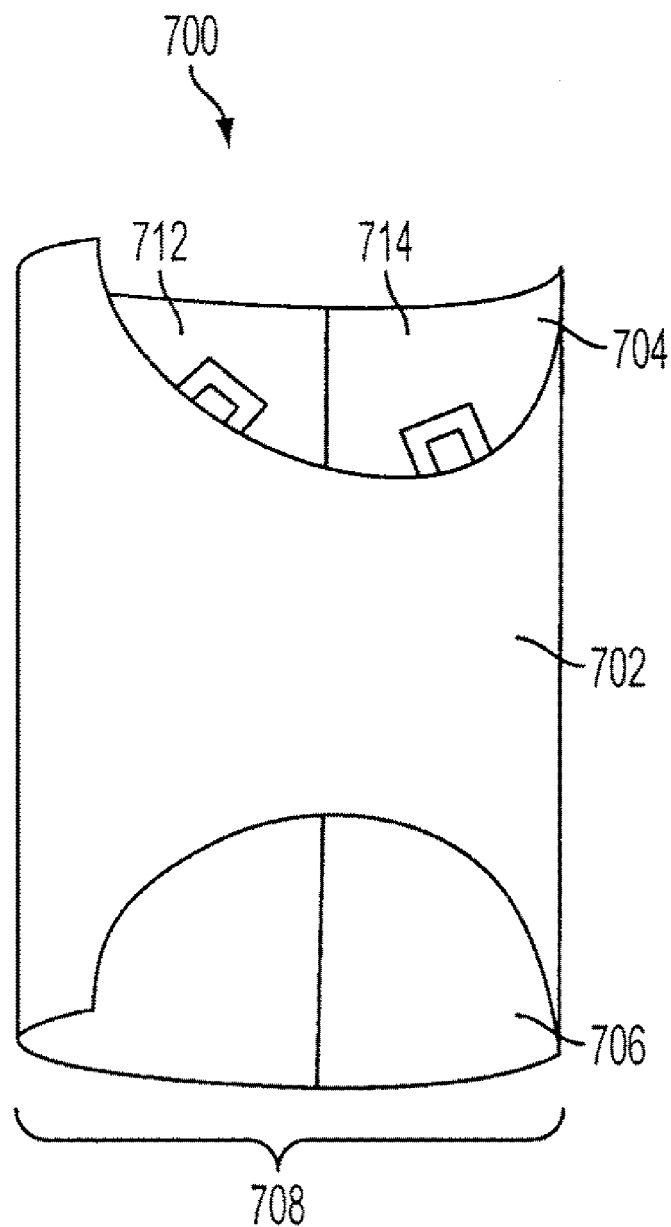
FIG. 7 is a view of a folded butterfly-shaped gastric skirt.

FIG. 7 is a view of a folded butterfly or step ladder-shaped gastric skirt 700. Once the distal end 712 and the proximal end 714 are connected together by coupling the connectors and receivers, a narrow surface 702 fits the lesser curvature of the stomach and is formed on one side of the gastric skirt 700 between indentation 704 and indentation 706. On the side opposite to the narrow surface 702 is the wide surface 708 which fits the greater curvature of the stomach.

In this embodiment, the narrow surface 702 of the butterfly-shaped gastric skirt 700 can be used to cover the lesser curvature of the stomach. Likewise, the broad surface 708 can be used to cover the greater curvature of the stomach.

In another embodiment, instead of having connectors and receivers to couple the gastric skirt 700, the distal end 712 and the proximal end 714 can be sutured or stapled together.

Figure 8A:
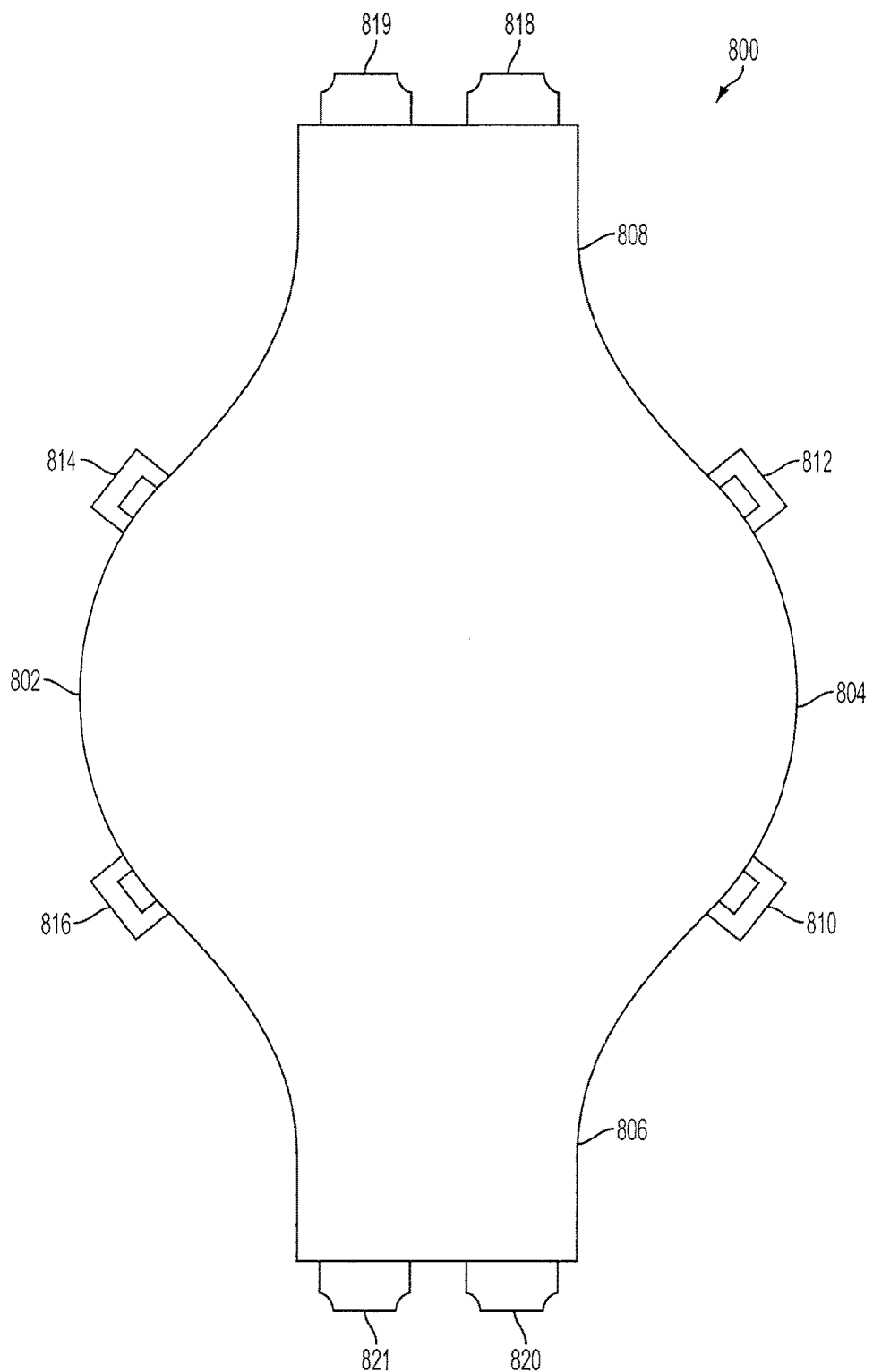
FIG. 8A is a view of a laid-open oval or pear-shaped skirt.

FIG. 8A is a view of a laid-open oval or pear-shaped skirt 800. In this embodiment, the gastric skirt 800 has a protrusion 802 on one side and a protrusion 804 on the opposing side. The proximal end 806 includes female connectors 820 and 821, and the distal end 808 includes male connectors 818 and 819. Therefore, when the gastric skirt 800 is folded, the proximal end 806 and the distal end 808 can be connected by securing the male connectors 818 and 819 into the female connector 820 and 821, respectively. In an embodiment, the width of the proximal end 806 and the distal end 808 is from about 4 centimeters to about 6 centimeters and the width between the protrusion 802 and the protrusion 804 is from about 8 centimeters to about 14 centimeters.

Outward protrusions 802 and 804 can be any shape, and not limited to, an oval, pear or semicircular shape as shown in FIG. 8A. For example, each of the outward protrusions 802 and 804 can be formed in the shape of a square, a triangle, or any other shape. The size of each outward protrusion 802 and 804 can also be varied in order to provide an optimal fit around the stomach. Furthermore, the outward protrusions 802 and 804 do not necessarily have to be the same shape or size as one another. Optional wings 810 and 812 may be attached to outward protrusion 804, and optional wings 814 and 816 may be attached to outward protrusion 802. In another embodiment, the gastric skirt 800 can have no wings attached, or wings only on one side.

Figure 8B:
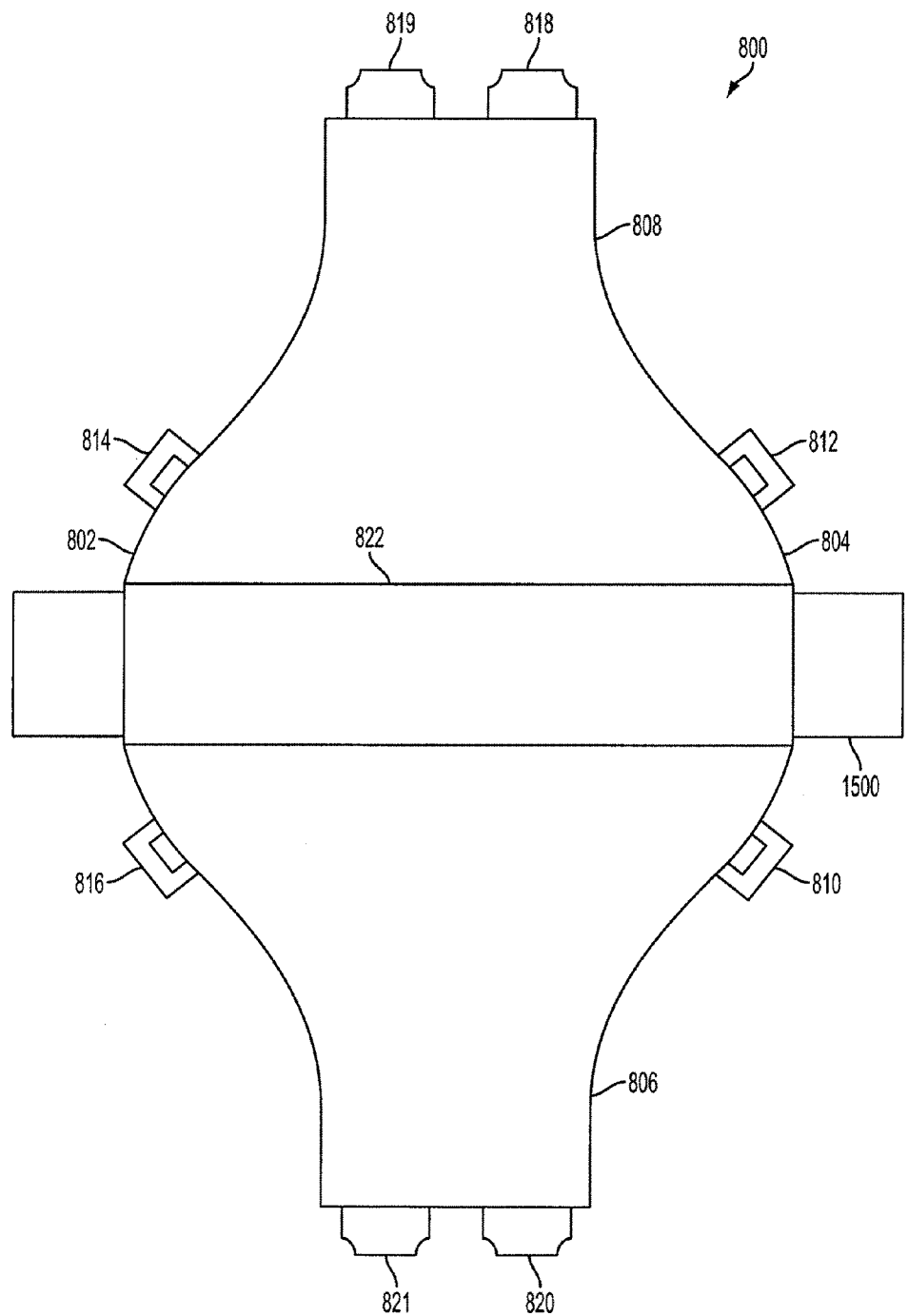
FIG. 8B is a view of a laid-open oval or pear-shaped skirt having a pouch that holds a balloon.

FIG. 8B is a view of a laid-open oval or pear-shaped skirt 800 having a pouch 822 that holds a balloon 1500. When the skirt 800 is wrapped around the stomach, the balloon 1500 can be secured in the pouch 822 or be inserted into the pouch 822 to keep the tucked-in portion within the stomach.

Figure 8C:
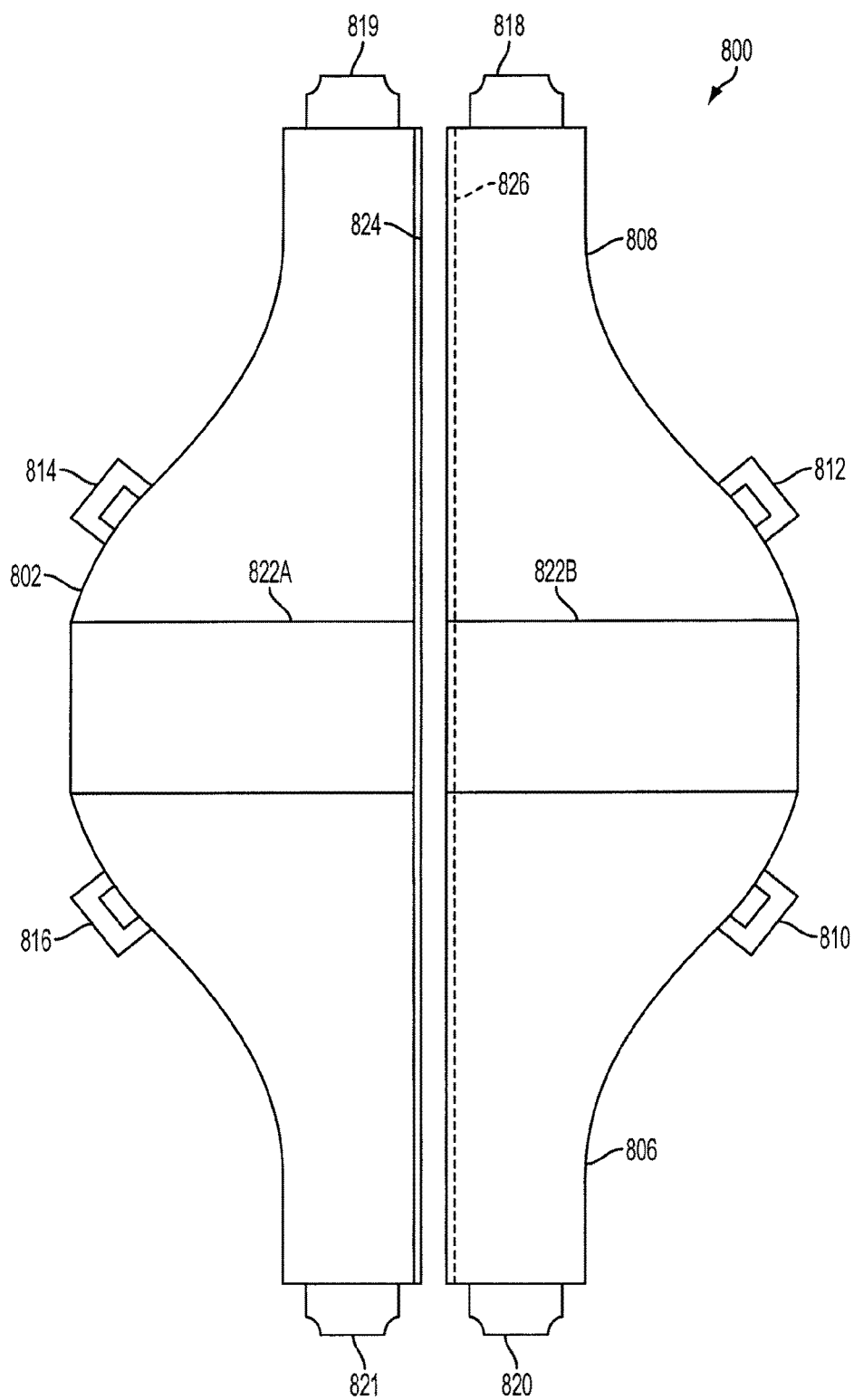
FIG. 8C is a view of a modular laid-open oval or pear-shaped skirt having a pouch that holds a balloon.

FIG. 8C is a view of a modular laid-open oval or pear-shaped skirt 800 having a pouch 822A and 822B that holds a balloon. The modular gastric skirt 800 may have two or more strips or modules. Each strip may have a ridge 824 and/or a groove 826 for attachment to adjacent strips. The ridge 824 securely fits into the groove 826 along the length of each strip to prevent unwanted detachment of adjacent strips and any in-growth of tissue between adjacent strips. The pouch 822 comprises two pieces 822A and 822B since the skirt 800 is modular.

FIG. 9A is a view of a folded gastric skirt 900 with locking clips. The gastric skirt 900 includes a proximal end 903 and a distal end 905. When the gastric skirt 900 is folded so that the proximal end 903 and the distal end 905 connect, a hollow shaped gastric skirt 900 is formed with a skirt body 902. Each locking clip comprises a male connector 904, 906, or 908, and a corresponding female receiver 914, 912, or 910, respectively. A right wing 916 and a left wing 918 are placed on opposite sides of one end of the skirt body 902. The wings 916 and 918 are used to connect the gastric skirt 900 to a collar (see also FIG. 11).

FIG. 9B is a view of a locking clip for the gastric skirt 900 shown in FIG. 9A. The locking clip 920 comprises the male connector 908, which includes a hinge pin 922. The locking clip 920 also comprises the female connector 910. To engage the locking clip 920, the hinge pin 922 interlocks with an opening in the female connector 910. Once the male connector 908 and the female connector 910 are engaged, the locking clip 920 holds a portion of the skirt body together. Furthermore, the male connector 908 includes a lower portion 926 which extends outwards. The female connector 910 includes an upper portion 924 which also extends outwards. When the male connector 908 and the female connector 910 are engaged, the lower portion 926 rests underneath the upper portion 924.

Figure 10A:
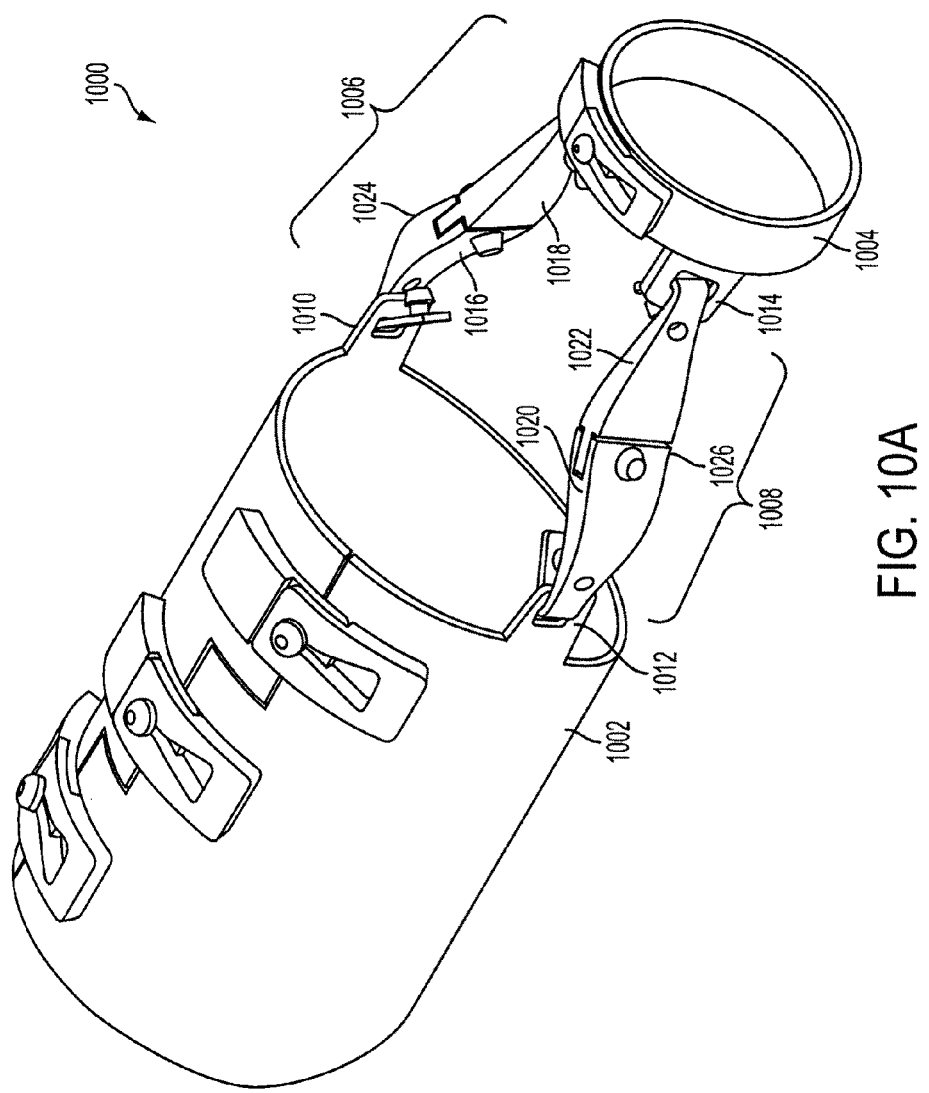
FIG. 10A is a view of a gastric skirt with a harness system.

FIG. 10A is a view of a gastric skirt 1002 with a harness system 1000. The harness system 1000 may include a gastric skirt 1002, an upper collar 1004, and connector straps 1006 and 1008. The gastric skirt 1002 is placed around the body of the stomach as previously described in FIG. 5A. In another embodiment, a lower collar (not pictured) is also included, allowing the upper collar 1004 and the lower collar to work in conjunction to hold the gastric skirt 1002 in position.

The upper collar 1004 is connected to the gastric skirt 1002 via the connector strap 1006 and the connector strap 1008, which are both, for example, connecting straps. The connector strap 1006 includes a skirt hook 1016 and a collar hook 1018. Likewise, the connector strap 1008 includes a skirt hook 1020 and a collar hook 1022. Regarding the connector strap 1008, the skirt hook 1020 connects to the gastric skirt 1002 at a wing 1012. The collar hook 1022 connects to the collar 1004 at a wing 1014. Regarding the connector strap 1006, the skirt hook 1016 connects to the gastric skirt 1002 at a wing 1010. The collar hook 1019 connects to the collar at a wing (not shown) located at a substantially parallel location as wing 1014 on the opposite side of collar 1004.

The connector strap 1006 has a flexible hinge 1024 to accommodate angulations to various anatomical differences where the skirt hook 1016 and the collar hook 1018 connect with each other. Likewise, the connector strap 1008 has a flexible hinge 1026 where the skirt hook 1020 and the collar hook 1022 connect with each other. The flexible hinges 1024 and 1026 help to accommodate any angulations of the stomach in relation to the lower esophagus and the fundus or the stomach and the pylorus, as well as help to accommodate the angles and contractility or peristaltic movements of the stomach.

Figure 10B:
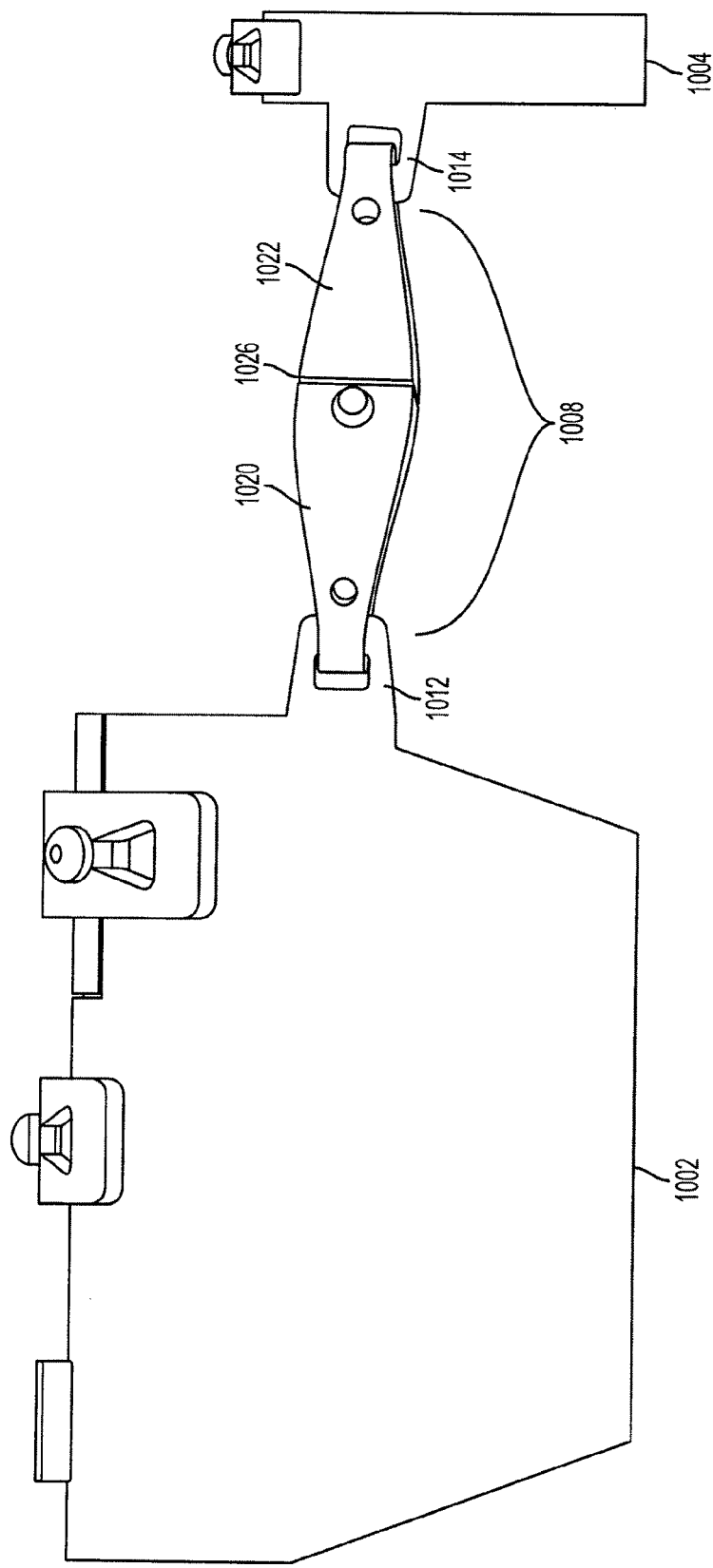
FIG. 10B is a side-view of a gastric skirt with a harness system.

FIG. 10B is a side-view of the gastric skirt 1002 with a harness system 1000. In an embodiment, the gastric skirt 1002, the upper collar 1004, the lower collar (not shown), the connector strap 1008, and the connector strap 1006, all have the same thickness and are all made of the same material. In an embodiment, this thickness is up to $\frac{1}{35,000}$th of an inch.

Figure 11:
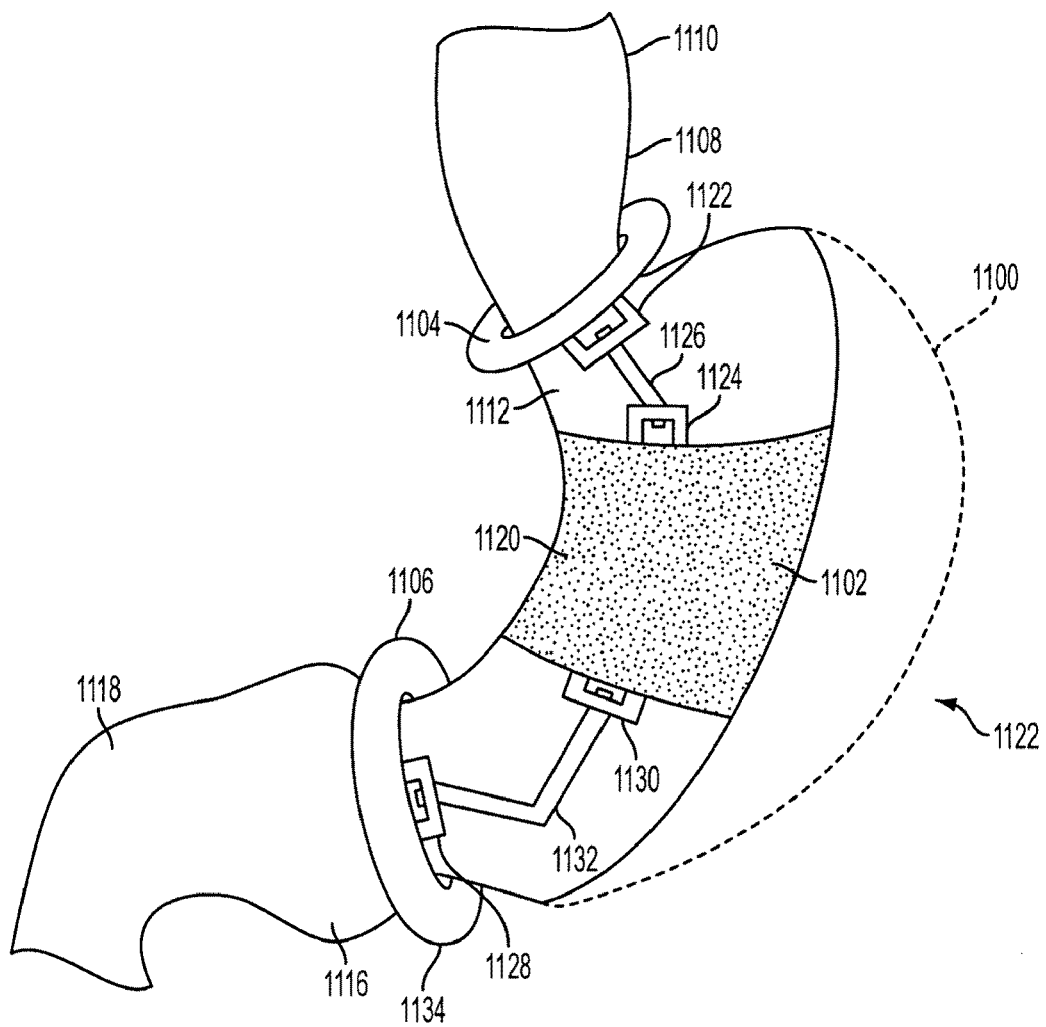
FIG. 11 is a view of a gastric wrap with a harness system in position around a stomach.

FIG. 11 is a view of a gastric skirt 1102 with a harness system in position around a stomach 1100. The gastric skirt 1102 is placed along the greater curvature 1122 and the lesser curvature 1120 of the stomach 1100. An upper collar 1104, also known as the cardia collar, is placed around the lower end of esophagus 1108 at a position near or adjacent to the cardiac notch 1112. The upper or cardia collar 1104 is large enough in diameter to encircle the lower esophagus 1108, but small enough so that it cannot encircle the larger diameter portion of the esophagus 1110. The upper collar 1104 is connected to the gastric skirt 1102 via a connector strap 1126. The connector strap 1126 is attached to the upper or cardia collar 1104 at a wing 1122, and the connector strap 1126 is attached to the gastric skirt 1102 at a wing 1124. This design prevents the upper collar 1104 from moving very high up the esophagus 1110, helps to hold the gastric skirt 1102 in place, and may help in reducing gastro esophageal reflux ("gastric reflux") or achalasia or dysphagia after the procedure.

The lower collar 1106, also known as the antral collar, is placed around a lower portion of the stomach near the angular notch 1134 at the pylorus 1116, also known as the pyloric antrum notch. The lower collar 1106 is large enough in diameter to encircle part of the lower portion of the stomach near the pylorus 1116, but small enough so that it cannot encircle the larger diameter portion of the small intestine 1118. The lower collar 1106 is connected to the gastric skirt 1102 via connector strap 1132. The connector strap 1132 is attached to the lower collar 1106 at a wing 1128, and connector strap 1132 is attached to the gastric skirt 1102 at a wing 1130. This design prevents the lower collar 1106 from moving down into the small intestine 1118, and helps to hold the gastric skirt 1102 in place. Furthermore, the lower collar 1106 may assist in slowing the gastric emptying from the stomach into the small intestine 1118. The lower collar 1106 may also assist in anchoring the gastric skirt 1102 in place.

In another embodiment, only the upper collar 1104 is attached to the gastric skirt 1102, and a lower collar 1106 is not present. As the volume of the fundus 1114 fills with food, the fundus 1114 stretches and expands, preventing the gastric skirt 1102 from sliding upwards. Thus, the lower collar 1106 may not necessarily be required in all patients to help hold the gastric skirt 1102 in place around the stomach 1100. Alternatively, in another embodiment, only the lower collar 1106 is attached to the gastric skirt 1102 and an upper collar 1104 is not present.

The gastric skirt 1102 and harness system are modular, and provides patients with at least three different options. In the first option, only the gastric skirt 1102 is utilized, without the collars 1104 and 1106 and the connector straps 1126 and 1132. In this embodiment, the healthcare professional may decide to not include the collars 1104 and 1106 if there is not a high risk of gastric reflux or achalasia, or if there is not a high risk that the gastric skirt 1102 may be displaced.

In the second option, the gastric skirt 1102 is utilized along with the collar 1104, but without the collar 1106 and without the connector straps 1126 and 1132. In this embodiment, the gastric skirt 1102 and the collar 1104 are not connected to each other. The healthcare professional may decide on this option if there is a risk of gastric reflux, achalasia, dysphagia but not a high risk that the gastric skirt 1002 or the collar 1104 may be displaced.

In the third option, the gastric skirt 1102 is utilized with the collars 1104 and 1106 and the connector straps 1126 and 1132. The healthcare professional may decide on this option if there is a risk of gastric reflux, or dysphagia and a risk of that the gastric skirt 1102 or collars 1104 and 1106 may be displaced. In this option, both the upper collar 1104 and the lower collar 1106 do not need be utilized, and only one of the collars 1104 or 1106 can be used. The upper collar 1104 not only serves to hold the gastric skirt 1102 in place, but is also a mechanism to help reduce gastric reflux and dysphagia.

The modular design allows the healthcare professional to decide which components of the gastric skirt system will be utilized, as well as the order of insertion of the various components.

In an embodiment, the upper collar 1104 and the lower collar 1106 each have a diameter from about 4 centimeters to about 6 centimeters. The upper collar 1104 can have a larger diameter up to about 11 centimeters in cases where the patient suffers from esophageal achalasia. In an embodiment, the length of the upper collar 1104 and the lower collar 1106 is up to about 4 centimeters.

The length of connector straps 1126 and 1132 can be varied to accommodate various stomach sizes. In a preferred embodiment, connector strap 1126 and connector strap 1132 have a length of about 5 centimeters.

The gastric skirt 1102 can have a length of about 6 centimeters to about 14 centimeters. In a preferred embodiment, the length of the gastric skirt 1102 is from about 8 centimeters to about 12 centimeters. The width of the greater curvature side of the gastric skirt 1102 is from about 7 centimeters to about 10 centimeters, and the width of the lesser curvature side of the gastric skirt 1102 is from about 3 centimeters to about 5 centimeters.

Some patients who undergo various gastric banding procedures experience gastric reflux, and it is believed that gastric banding procedures may cause or aggravate gastric reflux. Gastric reflux occurs when irritating stomach contents, such as acid, accumulate in the stomach outside of the lower esophagus entrance, and eventually, leak or regurgitate back into the esophagus. This leakage, over time, causes the lower esophagus to lose its tone, leaving the lower esophagus entrance poorly controlled, tortuous, unconstructed or floppy.

The upper collar 1104 may be approximately the same size as the lower esophagus or may be slightly larger. Once in position, the upper collar 1104 applies support by forming a significant wrap around the lower end of the esophagus 1108 or the cardia. The upper collar 1104 restricts the lower end of the esophagus opening 1108 and attempts to minimize regurgitation, thereby reducing gastric reflux.

Figure 12:
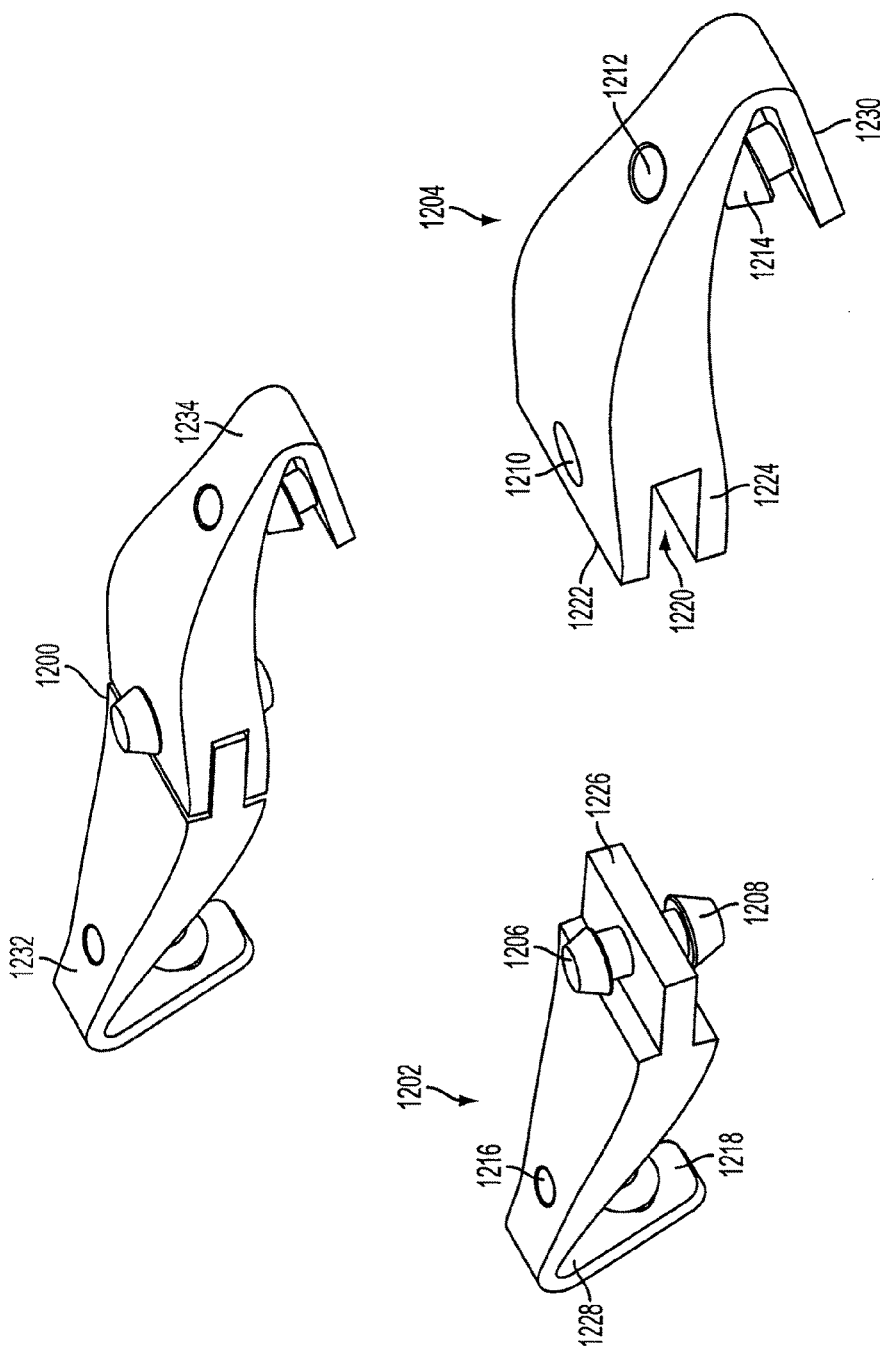
FIG. 12 is a view of an exemplary connector.

FIG. 12 is a view of an exemplary connector strap. The connector strap 1200 has a lower portion 1232 and an upper portion 1234. The lower portion 1232 corresponds to the skirt hook 1202. The upper portion 1234 corresponds to the collar hook 1204. The connector strap 1200 has a skirt hook 1202 and a collar hook 1204. The skirt hook 1202 includes hinge pin 1206, hinge pin 1208, and extending portion 1226. The collar hook 1204 includes a hole 1210 through ridge 1222 and a second hole (not shown) through ridge 1224. The collar hook 1204 also includes a cavity 1220. The hinge pins 1206 and 1208 are smaller in diameter than the diameters of hole 1210 and the second hole through ridge 1224. This design allows increased flexibility as the hinge pins 1206 and 1208 have space to re-position with their respective holes when the connector strap 1200 is rotated or shifted.

To connect the skirt hook 1202 and the collar hook 1204 together, hinge pin 1206 is inserted into hole 1210, and hinge pin 1208 is inserted into the second hole through ridge 1224. The extending portion 1226 is inserted into the cavity 1220. Once the skirt hook 1202 and the collar hook 1204 are connected, the connector strap 1200 is formed.

The skirt hook 1202 also includes hole 1216 and hinge pin 1218. To attach the connector strap 1200 to a wing (not shown) on the gastric skirt (not shown), the wing is placed inside the hinge cavity 1228 so that hinge pin 1218 is inserted through the wing. To secure the wing to the skirt hook 1202, the hinge pin 1218 is pushed through the hole 1216. The hinge pin 1218 has a triangular shape, with a narrow top and a wide base. The diameter of the base of the hinge pin 1218 is larger than the diameter of hole 1216. This design allows the hinge pin 1218 to be securely fastened once it is inserted through hole 1216. Likewise, the collar hook 1204 includes a hole 1212, a hinge pin 1214, and a hinge cavity 1230 to secure the collar hook 1204 to a wing on the collar (not shown).

In an embodiment, the connector strap 1200 is made of an elastomer, such as silicone. However, the connector can be made from other types of elastomers or thermoplastic polymers, ePTFE, Dacron®, or any combination thereof.

Figure 13A:
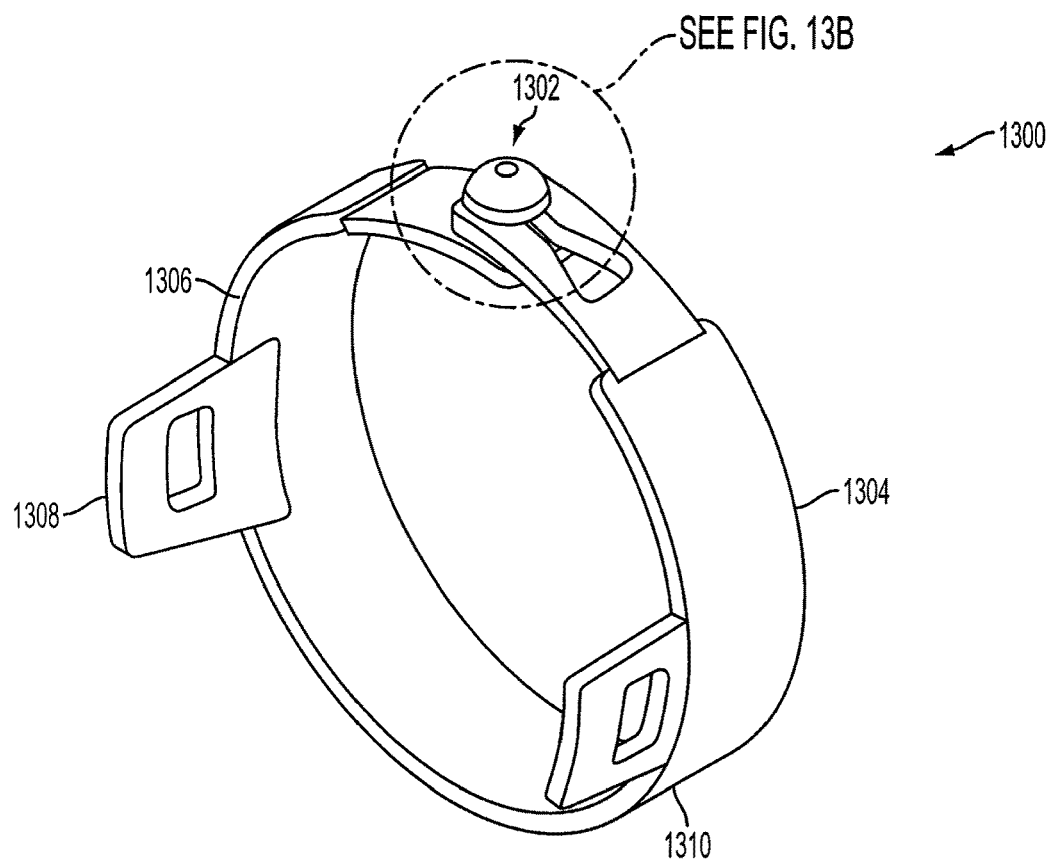
FIG. 13A is a view of a collar with wings.

FIG. 13A is a view of a collar. The collar 1300 includes a locking clip 1302. The collar 1300 has a distal end 1304 and a proximal end 1306. The distal end 1304 and the proximal end 1306 are connected by the locking clip 1302. The collar 1300 further includes a first wing 1308 and a second wing 1310 that are used to secure the collar 1300 to the gastric skirt connector strap (not shown).

In order to place the collar 1300 around the lower esophagus or cardia, the locking clip 1302 is not engaged, so that the distal end 1304 and the proximal end 1306 are laid open. The collar 1300 is then fitted around a portion of the lower esophagus as described above. Once the collar 1300 is in place, the locking clip 1302 is engaged by connecting the distal end 1304 and the proximal end 1306 together.

Figure 13B:
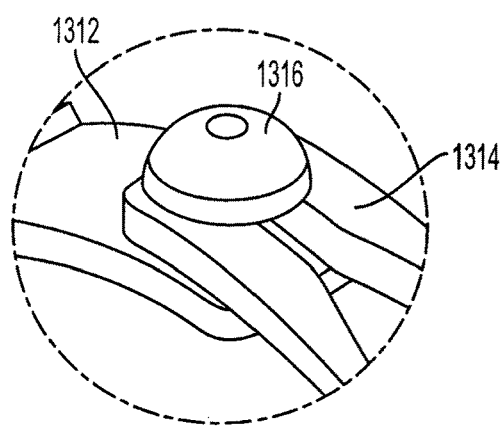
FIG. 13B is a view of a locking clip for a collar.

FIG. 13B is a view of a locking clip for a collar 1300. The male connector 1312 includes a hinge pin 1316 which interlocks with an opening in the female connector 1314. Once the male connector 1312 and the female connector 1314 are engaged, the locking clip holds the collar in position.

Figure 13D:
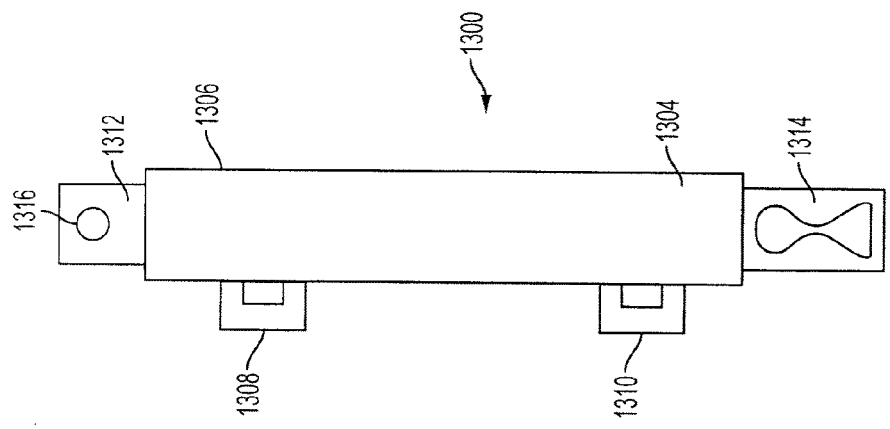
FIG. 13D is a view of a laid-open collar.
Figure 13C:
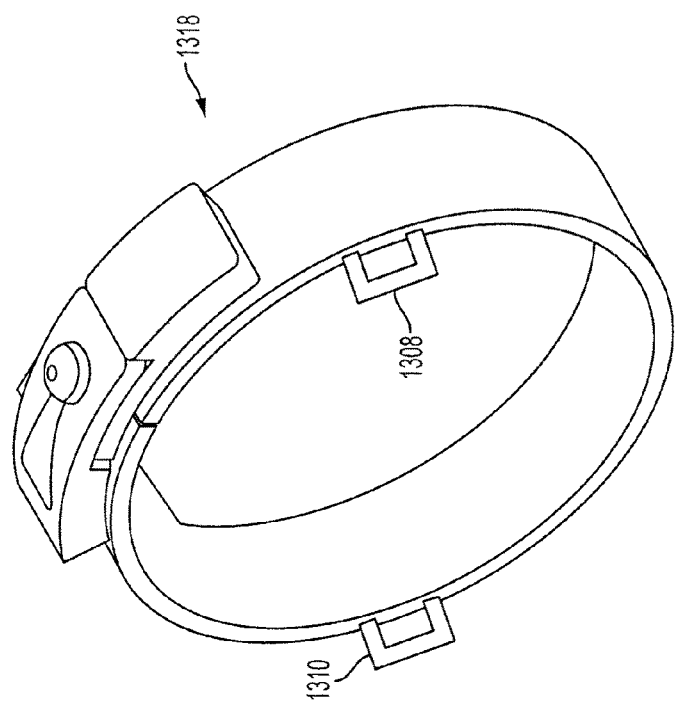
FIG. 13C is a view of a collar without wings.

FIG. 13C is a view of a collar 1300 without wings. The collar 1318 is used when a collar is not required to be connected to the gastric skirt (not shown), such as in surgical option one discussed above.

The locking clip 1302 can be any type of locking, coupling, or clasping mechanism, and is not limited to the male connector 1312 and female connector 1314 designs shown in FIGS. 13A-D. For example, the male connector may be an insertable clip, and the female connector can include an opening to receive and secure the insertable clip. In another embodiment, the clip can slide in and out of the body of the skirt, and can have an elastic component that stretches to accommodate the size and shape of the stomach.

In an embodiment, the collar 1300 and locking clip 1302 are made from a composition of silicone and PTFE/ePTFE. However, the collar 1300 and locking clip 1302 can be made from other elastomers or thermoplastic polymers, or any combination thereof.

In another embodiment, the distal end 1304 and proximal end 1306 can be sutured or stapled together at the time of positioning by the healthcare professional.

In yet another embodiment, the collar 1300 can be shaped as a semicircular ring, or in a "C" shape, and be made of a memory-retaining material. Once the collar 1300 is placed around a portion of the lower esophagus, it retains its shape. Thus, a locking clip is not required.

FIG. 13D is a view of a laid-open collar 1300. The collar 1300 is in a strap form when the male connector 1312 and the female connector 1314 are not connected.

As described above and shown in FIG. 1B, a portion of the stomach is tucked inwards prior to application of the gastric skirt around the stomach.

Figure 14:
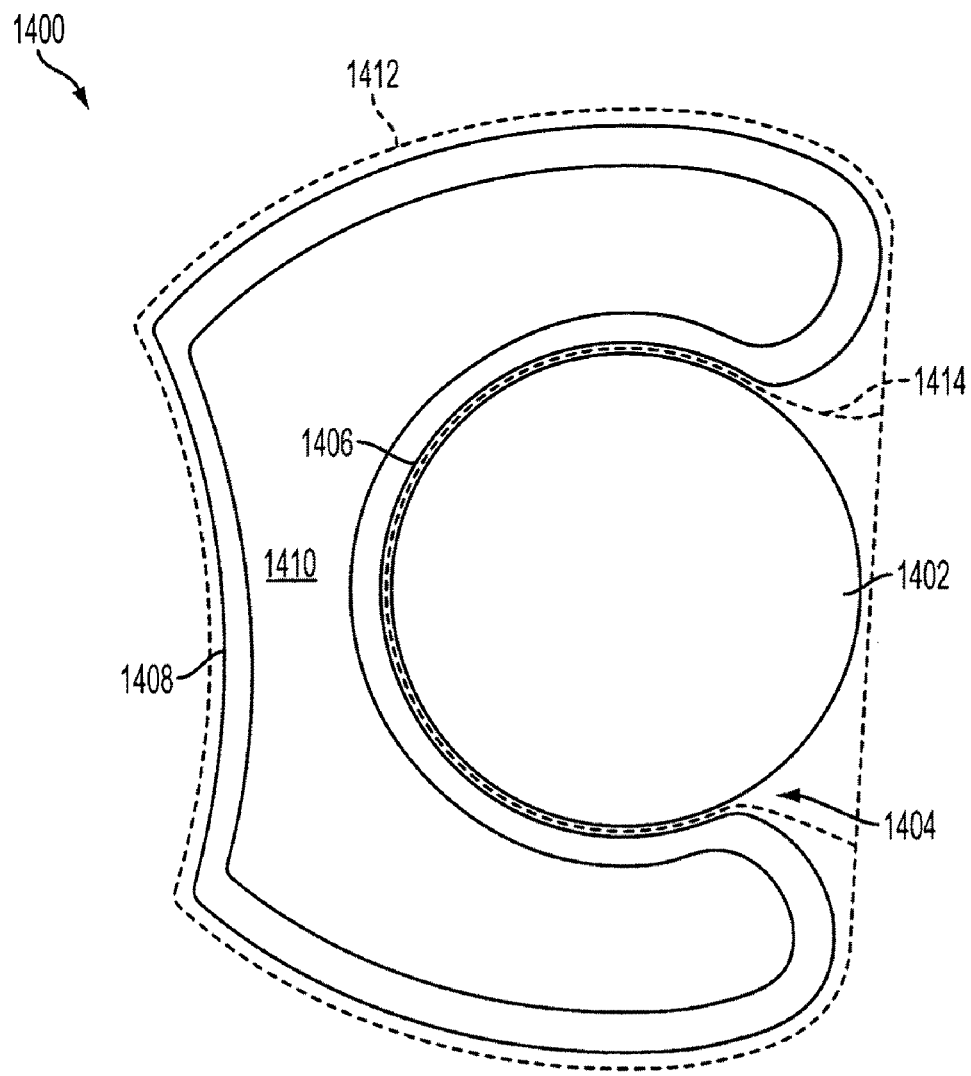
FIG. 14 is a cross-sectional view of a stomach and a balloon positioned within a greater curvature of the stomach when the greater curvature is tucked into the stomach.

FIG. 14 is a cross-sectional view of a stomach 1400 and a balloon 1402 positioned within a greater curvature 1406 of the stomach 1400 when the greater curvature 1406 is tucked into the stomach 1400. In an embodiment, after the greater curvature 1406 of the stomach 1400 is tucked inwards, a cavity 1404 is formed as a result of the tucking procedure and a balloon 1402 is placed within the cavity 1404, which can be left open, and a gastric skirt 1412 is tightly positioned around the stomach 1400 to hold the balloon 1402 in place within the cavity 1404. Hence, the balloon 1402 is placed within the tucked-in portion of the stomach 1400. Alternatively, the balloon 1402 may be placed within a pouch 1414 that is attached to the gastric skirt 1412. The greater curvature 1406 of the stomach 1400 is pushed inwards to reduce the inner volume 1410 of the stomach 1400. The balloon 1402 applies pressure against the greater curvature 1406 of the stomach 1400 and helps to maintain the shape of the cavity 1404. Following the placement of the balloon 1402, the gastric skirt 1412 is placed around the stomach 1400 as described above. In this embodiment, when the gastric skirt 1412 is positioned around the stomach 1400, the connectors as shown in FIG. 5B connect with one another along the lesser curvature 1408 of the stomach 1400.

As described above, the greater curvature 1406 of the stomach 1400 is the preferred tucking portion. However, the tucked-in portion of the stomach 1400 may be a portion of the lesser curvature 1408, or any portion of the stomach 1400 not along either the greater curvature 1406 or the lesser curvature 1408. If the tucked-in portion of the stomach 1400 is along the lesser curvature 1408, then the connectors as shown in FIG. 5B connect with one another along the greater curvature 1406 of the stomach 1400.

Figure 15A:
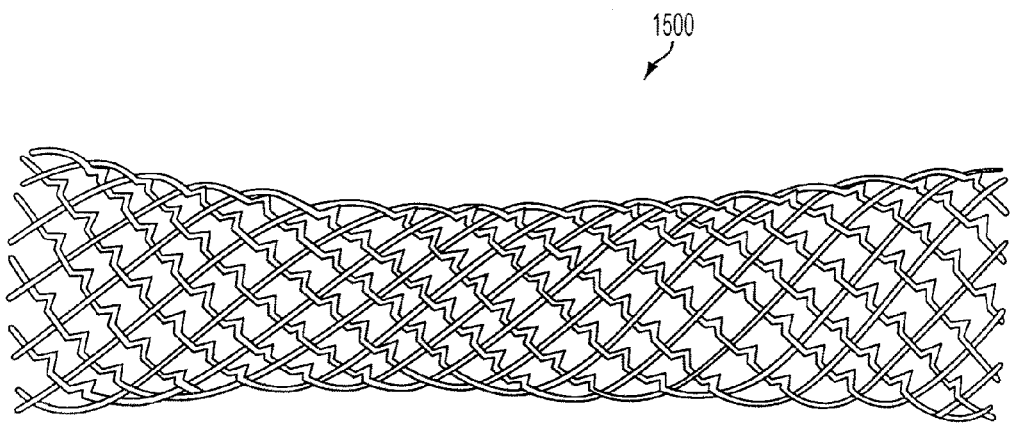
FIG. 15A is a view of the balloon of FIG. 14.

FIG. 15A is a view of the balloon of FIG. 14. The balloon 1500 can be a sealed or open ended stent, cylindrical air filled or saline filled device with an ePTFE, Dacron®, or silicon coating or covering. The balloon 1500 is preferably made of an alloy of nickel and titanium (Nitinol) or stainless steel wire cage which provides the balloon 1500 with a self-expanding memory. The unique characteristic of this alloy, known generally as "Nitinol," is that it has a thermally triggered shape memory. This allows the balloon cage to be crimped per a desired length, width, and volume based on the balloon size required per patient's stomach dimensions, and then the balloon 1500 is crimped into a sheath so that it can fit through a trocar (not shown). The balloon 1500 regains its desired shape when deployed at room temperature, such as the temperature of the human body or outer stomach lining.

The semi-rigid or rigid Nitinol or stainless steel wire frame is covered with ePTFE, silicone, Dacron® or any other elastomer or thermoelastic elstomer, nitinol cage. The balloon 1500 provides support to the outer lining of the stomach when the balloon 1500 is placed in position within the cavity 1404 of FIG. 14. The desired shape of the balloon 1500 is retained even under pressure from the stomach lining or the gastric skirt (not shown) since Nitinol or stainless steel or titanium wire cage is rigid and has memory. After the balloon 1500 is placed in position, the gastric skirt is placed around the stomach as described above.

In one embodiment, the self-expanding nitinol cage or stainless steel wire cage balloon 1500 is covered with silicone, and is formed in the shape of a cylindrical balloon, and can have open or closed ends. In another embodiment, the self-expanding nitinol ballon 1500 is covered with ePTFE, and can have open or closed ends.

Figure 15B:
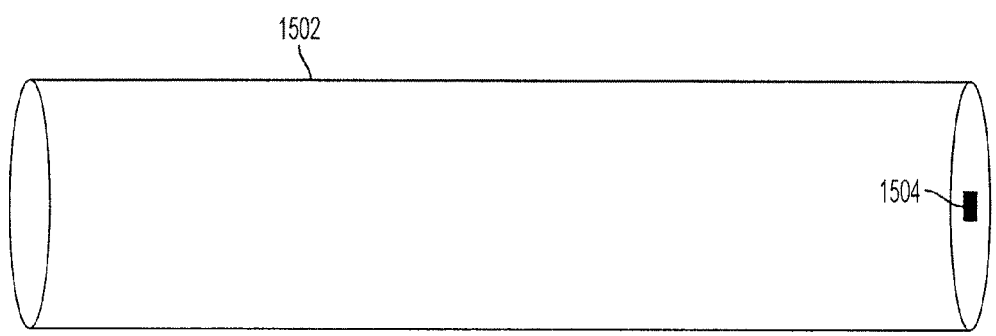
FIG. 15B is a view of a sealed balloon with a port.

FIG. 15B is a view of a balloon 1502 with a port 1504. The balloon 1502 is made entirely of silicone, other elastomers, thermoplastic polymers, or any combination thereof, and may be filled with air or liquid (e.g., saline) and methylene blue and has a closed end and a port 1504 to inject air, liquid or methylene blue. The methylene blue is used to detect leaks of the balloon 1502.

The balloon 1500 has a length of about 7 centimeters to about 10 centimeters. In an embodiment, the diameter of the balloon 1500 is from about 1 centimeter to about 3 centimeters. However, the diameter of the balloon 1500 can be adjusted by the healthcare professional based on the amount of stomach that is tucked-in.

Figure 16:
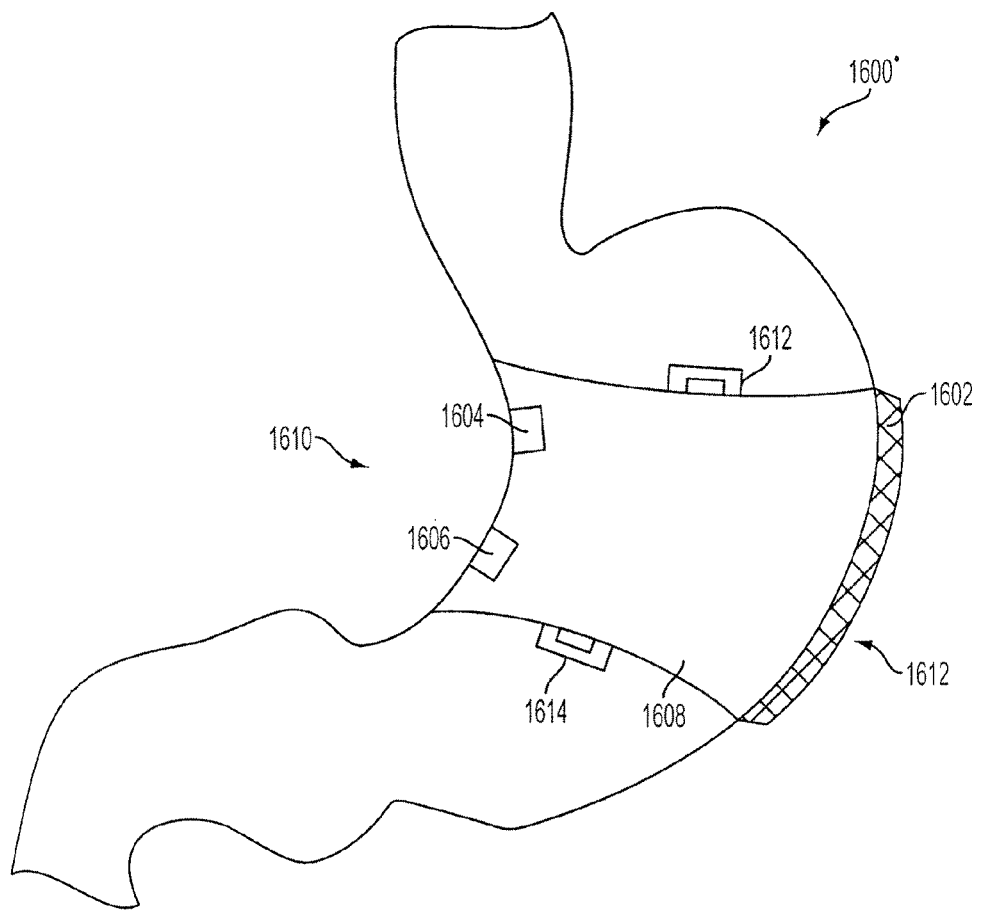
FIG. 16 is a view of the gastric wrap of FIG. 6 and the balloon in position around a stomach.

FIG. 16 is a view of the gastric skirt of FIG. 6 and the balloon in position around a stomach. As seen in FIG. 16, connectors 1604 and 1606 are positioned on the lesser curvature side 1610 of the stomach 1600. Balloon 1602 is positioned on the greater curvature side 1612 of the stomach 1600. In this embodiment, the connectors 1604 and 1606 are not on the greater curvature side 1612 so that there is room for the balloon 1602 to be retained and held in place by the gastric skirt 1608 within the tucked-in portion (not shown) of the stomach.

Furthermore, optional wings 1612 and 1614 are attached to the gastric skirt 1608 to attach the gastric skirt 1608 to collar connector straps (not shown).

Figure 17:
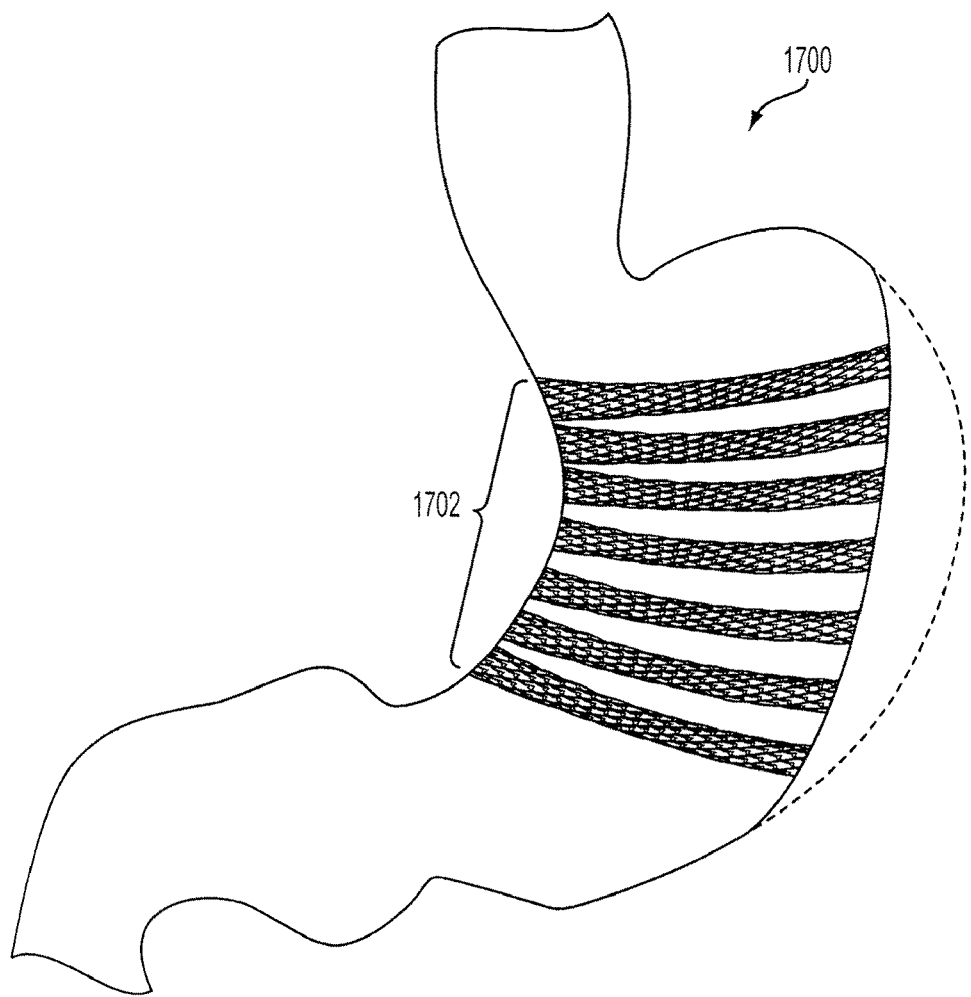
FIG. 17 is a view of one or more ropes wrapped around a tucked-in stomach.

FIG. 17 is a view of one or more ropes 1702 wrapped around a tucked-in stomach 1700. The ropes 1702 may be made of a biodegradable material or a woven silicon material or any other material described herein. The stomach 1700 is tucked-in and then the ropes 1702 are wrapped around the stomach 1700. Each rope 1702 can be a silicone rope, a mesh made of biodegradable elastomer, a metal, an alloy, a silicone or thermo-elastic material to harness the stomach or to create the pouch proximally or distal to the body of the stomach or to produce the same effect as the gastric skirt by tucking the stomach.

Figure 18:
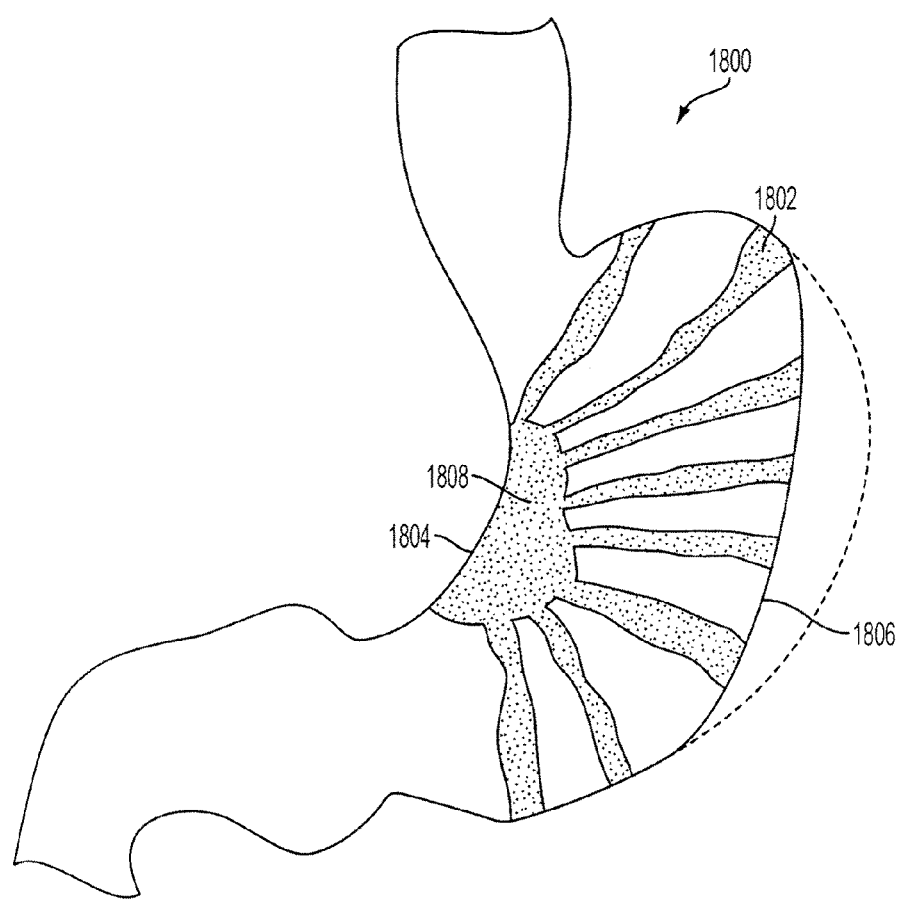
FIG. 18 is a view of one or more tentacles wrapped around a tucked-in stomach where the tentacles can be independently pulled and locked in place using a ring and clip system or a tie lock.

FIG. 18 is a view of one or more tentacles 1802 wrapped around a tucked-in stomach 1800 where the tentacles 1802 can be independently pulled and locked in place using a ring and clip system 1808 or a tie lock (not shown). Each tentacle 1802 can be independently tighten and loosened to control the tension. Each tentacle 1802 can be pulled through a ring or hole and the clip can lock the tentacle in place. The tentacles 1802 can be wrapped around the greater curvature 1806 and the lesser curvature 1804 of the stomach 1800. The tentacles 1802 can be any shape, such as straight or curved, and are not limited to the design shown in FIG. 18. Furthermore, the tentacles 1802 can be made of an expandable material originating from the body at the lesser curvature 1804 or the greater curvature 1806.

While the principles of the disclosure have been illustrated in relation to the exemplary embodiments shown herein, the principles of the disclosure are not limited thereto and include any modification, variation or permutation thereof.

What is claimed is:

1. A gastric restraining device for treating excessive weight or obesity in mammals, comprising:
    a skirt having a top portion, a bottom portion, a left portion of a predetermined width, a right portion of a predetermined width, and a central portion of a predetermined width located between the left portion and the right portion, the width of the central portion being less than the width of the left portion and the width of the right portion, the skirt adapted to be positioned around and in contact with an internal stomach organ of a mammal to tightly engage the internal stomach organ when the left portion is in proximity to the right portion;
    a first clip attached to the right portion of the skirt; and
    a second clip attached to the left portion of the skirt and adapted to engage the first clip and maintain the left portion in proximity to the right portion, the skirt or the first and second clips completely covering an entire area between the left portion and the right portion when the left portion is in proximity to the right portion and the first and second clips adapted to be positioned around a greater curvature of the internal stomach organ, thereby preventing expansion of the internal stomach organ when the first clip is fastened to the second clip.

2. The gastric restraining device of claim 1, further comprising a connecting strap having an upper portion and a lower portion, the lower portion of the connecting strap configured to be attached to the top portion of the skirt.

3. The gastric restraining device of claim 2, further comprising an upper collar configured to be attached to the upper portion of the connecting strap, the upper collar further configured to be placed around a lower esophageal/cardia portion of the mammal.

4. The gastric restraining device of claim 2, further comprising a collar configured to be attached to the bottom portion of the skirt via a second connecting strap, the collar further configured to be attached to a pyloric antrum notch portion of the stomach.

5. The gastric restraining device of claim 1, wherein the top portion has a concave edge and the bottom portion has a concave edge.

6. The gastric restraining device of claim 1, wherein the skirt is made of an implantable silicon material or an ePTFE material.

7. A gastric constriction or restraining device for treating excessive weight or obesity in mammals, comprising:
    an elastomeric sheet formed in the shape of a cylinder and having a top portion, a bottom portion, a left portion, and a right portion, the sheet configured to be wrapped around a tucked-in stomach of a mammal so that the left portion is in contact with the right portion when the sheet is wrapped around the stomach;
    a first connector attached to the right portion of the sheet;
    a second connector attached to the left portion of the sheet, the second connector attachable to the first connector;
    a connecting strap having an upper portion and a lower portion, the lower portion of the connecting strap configured to be attached to the top portion of the sheet; and
    a collar configured to be attached to the upper portion of the connecting strap, the collar further configured to be placed around a lower esophageal portion of the mammal; and
    a lower collar configured to be attached to the bottom portion of the sheet via a second connecting strap, the lower collar further configured to be attached to a pyloric antrum notch portion of the stomach.

8. The gastric constriction device of claim 7, wherein the sheet is made of silicone.

9. The gastric constriction device of claim 7, wherein the sheet is made of a biodegradable and absorbable polymer.

10. The gastric constriction device of claim 7, wherein the sheet has a parallelogram shape.

11. The gastric constriction device of claim 7, wherein the sheet has a thickness of up to $1/35,000$th of an inch.

12. The gastric constriction device of claim 7, wherein the first connector, the second connector, the connector strap, the collar, and the sheet have the same thickness.

13. A method for treating excessive weight or obesity in mammals by gastric constriction or restraining, comprising:
    tucking a portion of the greater curvature of a stomach inward to reduce the volume of the stomach body so that the tucked portion occupies a portion of the stomach;
    placing a balloon along the outer wall of the greater curvature of the stomach within the tucked-in portion;
    placing a flexible elastomeric sheet around the stomach so that a portion of the sheet encircles the stomach and covers the tucked-in portion;
    connecting two opposing ends of the sheet so that the sheet constricts a portion of the stomach around the greater curvature of the stomach and the lower curvature of the stomach;
    placing an upper collar around a lower esophageal portion of the stomach;
    placing a first connecting strap between the sheet and the upper collar;
    placing a lower collar near a pyloric lower end of the stomach; and
    placing a second connecting strap between the sheet and the lower collar.

14. The method of claim 13, wherein the method is a laparoscopic procedure.

15. The method of claim 13, wherein the method is an open-surgical procedure.

16. The method of claim 13, wherein the two opposing ends of the sheet are connected by inserting a male connector formed integrally with the sheet at a first location into a female connector formed integrally with the sheet at a second location opposite the first location so as to form the sheet into a circle around the stomach.

17. The method of claim 13, wherein the upper collar is placed around a cardiac notch portion of the stomach.

18. The method of claim 13, wherein the lower collar is placed around a pyloric antrum notch portion of the stomach.

19. The method of claim 13, wherein the stomach is tucked inwards so as to reduce the volume of the stomach body by the stomach itself.

* * * * *